(12) United States Patent
McIntyre et al.

(10) Patent No.: US 8,868,351 B2
(45) Date of Patent: Oct. 21, 2014

(54) ESTIMATION OF NEURAL RESPONSE FOR OPTICAL STIMULATION

(71) Applicant: The Cleveland Clinic Foundation, Cleveland, OH (US)

(72) Inventors: Cameron C. McIntyre, Cleveland, OH (US); Thomas J. Foutz, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/650,533

(22) Filed: Oct. 12, 2012

(65) Prior Publication Data

US 2013/0096891 A1    Apr. 18, 2013

Related U.S. Application Data

(60) Provisional application No. 61/546,807, filed on Oct. 13, 2011.

(51) Int. Cl.
*G01N 33/48* (2006.01)
*G01N 33/50* (2006.01)
*G06F 19/12* (2011.01)
*G06F 19/10* (2011.01)

(52) U.S. Cl.
CPC ........... *G06F 19/12* (2013.01); *G06F 19/10* (2013.01)
USPC .................................................. 702/19

(58) Field of Classification Search
CPC .......................... G06F 19/10; G06F 19/12
USPC ............................... 702/19; 703/11
See application file for complete search history.

(56) References Cited

U.S. PATENT DOCUMENTS

| | | |
|---|---|---|
| 2007/0043401 A1 | 2/2007 | John |
| 2007/0054319 A1 | 3/2007 | Boyden et al. |
| 2008/0085265 A1 | 4/2008 | Schneider et al. |
| 2009/0078875 A1 | 3/2009 | Benny et al. |
| 2009/0088680 A1 | 4/2009 | Aravanis et al. |
| 2009/0093403 A1 | 4/2009 | Zhang et al. |
| 2009/0118800 A1 | 5/2009 | Deisseroth et al. |
| 2010/0145418 A1 | 6/2010 | Zhang et al. |
| 2010/0190229 A1 | 7/2010 | Zhang et al. |
| 2010/0262212 A1 | 10/2010 | Shoham et al. |
| 2010/0268150 A1 | 10/2010 | Mohanty et al. |
| 2010/0292931 A1 | 11/2010 | Wang et al. |
| 2011/0027909 A1 | 2/2011 | Bartlett et al. |
| 2011/0040351 A1 | 2/2011 | Butson et al. |
| 2011/0054346 A1 | 3/2011 | Hausman et al. |
| 2011/0066407 A1 | 3/2011 | Butson et al. |

FOREIGN PATENT DOCUMENTS

| | | |
|---|---|---|
| WO | 2008/089003 A2 | 7/2008 |
| WO | 2009/072123 A2 | 6/2009 |
| WO | 2009/127705 A1 | 10/2009 |
| WO | 2009/131837 A2 | 10/2009 |
| WO | 2009/146361 A1 | 12/2009 |
| WO | 2009/148946 A2 | 12/2009 |
| WO | 2009/155369 A1 | 12/2009 |
| WO | 2009/155371 A1 | 12/2009 |
| WO | 2010/006049 A1 | 1/2010 |
| WO | 2010/009141 A1 | 1/2010 |
| WO | 2010/056970 A2 | 5/2010 |
| WO | 2010/089355 A1 | 8/2010 |
| WO | 2010/115207 A1 | 10/2010 |
| WO | 2011/005978 A2 | 1/2011 |

OTHER PUBLICATIONS

McIntyre et al. Critical Reviewsin Biomedical Engineering, 2002, 30,Issue 4-6 , p. 249-281.*
PCT International Search Report, PCT/US2012/059939, mailed Mar. 26, 2013, pp. 1-11.
Pulver, Stefan R. et al. Temporal Dynamics . . . in *Drosophila* Larvae, J. Neurophysiol 101: 3075-3088, 2009.

* cited by examiner

*Primary Examiner* — Michael Borin
(74) *Attorney, Agent, or Firm* — Tarolli, Sundheim, Covell & Tummino LLP

(57) ABSTRACT

This disclosure relates generally to systems and methods for estimating a volume of tissue directly influenced (VTDI) by optogenetic stimulation. The systems and methods can also enable a user to quantitatively predict the spread of stimulation (e.g., action potential) resulting from optical stimulation in a patient's tissue.

30 Claims, 14 Drawing Sheets

ESTIMATION OF NEURAL RESPONSE FOR OPTICAL STIMULATION

CROSS-REFERENCE TO RELATED APPLICATION

This application claims the benefit of U.S. Provisional Patent Application No. 61/546,807, filed Oct. 13, 2011, and entitled ESTIMATION OF NEURAL RESPONSE FOR OPTICAL STIMULATION, the contents of which is incorporated herein in its entirety.

GOVERNMENT FUNDING

This invention was made with government support under Grant No. NIH R01 NS047388. The U.S. government may have certain rights in the invention.

TECHNICAL FIELD

This disclosure relates generally to systems and methods for determining a target volume of tissue influenced by optical stimulation.

BACKGROUND

Optogenetics is the combination of genetic and optical methods to control specific events in targeted cells of living tissue, even within freely moving mammals and other animals, with the temporal precision (millisecond-timescale) needed to keep pace with functioning intact biological systems. One application of optogenetics relates to neural stimulation. However, questions remain on the most efficient techniques to alter neural activity with photon sensitive ion channels, and quantitative tools to predict the spread of optical stimulation are lacking.

SUMMARY

This disclosure relates generally to systems and methods for determining a target volume of tissue influenced by optical stimulation.

In one example, a computer-implemented method can include storing, in memory, an estimated volume of distribution in tissue for a viral vector designed to express a light-responsive protein. An estimate of a volume of tissue directly influenced (VTDI) can be computed, by a processor, based on the estimated volume of distribution in tissue according to a light-neuron model. The light-neuron model can include a computational model that includes parameters representing at least one of properties of a neuron, a light responsive ion channel or pump, and a light source.

In another example, a non-transitory computer-readable medium includes instructions executable by a processor. The instructions can include a computational light-neuron model that includes a multi-compartment neuron model and a multi-state ion channel model or ion pump model, which is inserted into the axon model. The ion channel or pump model can include parameters representing states and transitions. The light-neuron model also includes a light distribution model that parameters irradiance from a light source on the neuron model. An estimator is programmed to evaluate an estimate of a volume of tissue directly influenced (VTDI) over a set of model parameters and compute a set of output parameters based on a comparison of the estimated VTDI with a target VTDI. The output parameters can be stored in memory.

DETAILED DESCRIPTION

This disclosure relates generally to systems and methods for estimating a volume of tissue directly influenced (VTDI) by optogenetic stimulation. The systems and methods further enable a user to quantitatively predict the spread of stimulation (e.g., action potential) resulting from optical stimulation in a patient's tissue. As used herein, the patient can be a human or other animal patient (e.g., mouse, primate or the like). The tissue being subjected to optogenetic stimulation can be any tissue of a patient in which an action potential can propagate, such as including the brain, heart or other muscle, spinal cord, peripheral nerves, optic nerves and the like.

Figure 1:
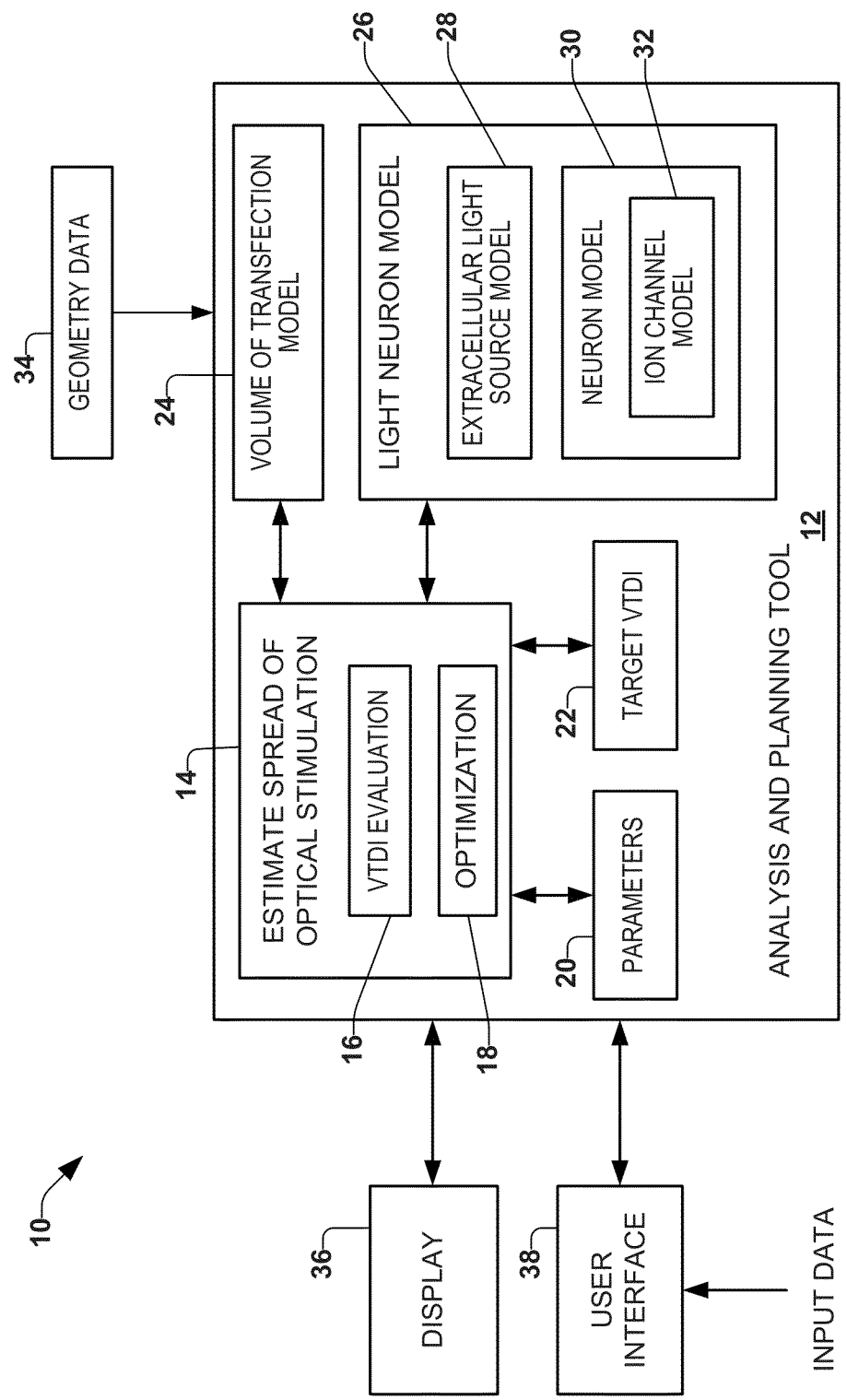
FIG. 1 depicts an example of a system that can be utilized to estimate a volume of tissue directly influenced by optical stimulation.

FIG. 1 depicts an example of a system 10 that can be utilized to facilitate analysis and planning for optogenetic stimulation. The system 10 includes an analysis and planning tool 12 that can be implemented as computer executable instructions stored in memory (e.g., computer readable media) and which can be executed by a processor. The analysis and planning tool 12 includes instructions, shown as estimation method 14, programmed to compute an estimation of the spread of optogenetic stimulation and corresponding parameters.

Opotogenetic stimulation is a form of optical stimulation technology that induces action potential in genetically altered cells. Specific types of neurons can be genetically targeted to provide for selective expression of light responsive protein (e.g., microbial opsins) that can provide activation potentials in selected neurons in response to light. For example, the opsin gene can be combined with a particular promoter to be active with only one or more types of neurons or other types of cells. The modified gene is inserted into a viral vector (e.g., a lentivirus, retrovirus, adenovirus or other) and inserted into tissue to target a specific cell type depending on promoter. The virus transfects the targeted cells to express light-responsive protein that can initiate an action potential via a corresponding ion channels or light-driven ion pump in response to optical stimulation with a light source. In other examples, the expression of light-responsive protein that can be provided to inhibit an action potential via a corresponding ion channels or light-driven ion pump in response to optical stimulation.

The tool 12 provides a researcher or clinician with information to configure and control optogenetic stimulation process intended to achieve a desired therapeutic effect for a given patient. For example, the tool 12 can assist a user with selection of a light-responsive protein, selection of a target volume, fluid delivery parameters to infusing the viral vector, selection of a light source and setting optical stimulation parameters.

The estimation method 14 can estimate the spread of optical stimulation to include a volume of tissue directly influenced (VTDI) by optical stimulation. In order to select appropriate optical stimulation parameters, an evaluation method 16 can be programmed to calculate and evaluate an action potential through an ion channel or ion pump in tissue in response to optical stimulation. The estimation method 14 can also includes an optimization process 18 that is programmed to ascertain a set of parameters 20 associated with the optogenetic stimulation process to achieve a target VTDI indicated at 22. The target VTDI 22 can be a user-defined volume or the target VTDI can be calculated by the tool 12 (or by an external method) for a given patient based on a desired therapeutic effect that is to be achieved by the optogenetic stimulation. For example, the target VTDI 22 can be provided to define a volume of tissue in a generic atlas brain, which can be mapped to the given patient based on corresponding geometry data 34 acquired for the given patient via a suitable imaging modality (e.g., MRI, CT and the like).

In the example of FIG. 1, the analysis and planning tool 12 includes a plurality of models for different phases or stages of the optogenetic stimulation process. As an example, the tool 12 can include a volume of transfection model 24 corresponding to delivery of fluid into tissue as well as transfection of cells in response to delivery of a viral vector. The volume of transfection model 24 thus can employ a variety of parameters within the parameter space 20, including type of delivery device (e.g., the catheter), trajectory of the delivery mechanism, flow rate, backflow rate, duration and transport of the virus. The volume of transfection model 24 thus can employ the fluid delivery parameters and the target VTDI 22 to optimize for the delivery parameters via the optimization routine 18 to achieve the target VTDI 22.

A corresponding volume of transfection can be calculated from simulation and a simulated volume of transfection utilized by the estimation method 14 to estimate the spread of the optogenetic stimulation. Alternatively or additionally, the simulated volume of transfection can be utilized to control delivery parameters for delivering the vector virus into tissue to achieve the target VTDI. An actual volume of distribution can be calculated and confirmed by imaging data such as in response to markers or tags being employed with the vector virus (see e.g., FIG. 6). The volume of transfection can also be confirmed in a similar manner by configuring the virus to express markers or tags. For example, imaging can be utilized to locate an actual volume of distribution for the viral vector and the transfection model 24 can be utilized to estimate the corresponding transfection of cells. This estimated volume of transfection (e.g., simulated and/or based on imaging) can be utilized in conjunction with a light neuron model 26 to calculate an estimated spread of optical stimulation and associated stimulation-related parameters.

In the example of FIG. 1, the light neuron model 26 can include an extracellular light source model 28 and a neuron model 30. The neuron model 26 further can contain a light-sensitive ion channel or ion pump model 32.

Figure 2:
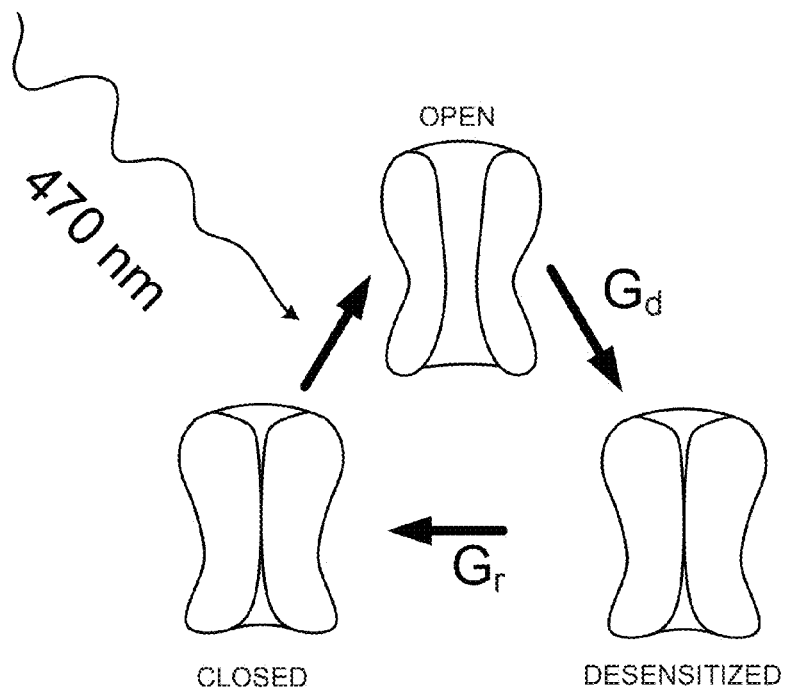
FIG. 2 depicts an example of a state diagram model of an ion channel in response to illumination.

As an example, FIG. 2 demonstrates an ion channel model for a channelrhodopsin, one example being channelrhodopsin-2 (ChR2) such as can be implemented as the model 32 of FIG. 1. While many of the following examples are described in the context of using ChR2, it will be understood that other light responsive proteins or opsins can be utilized without departing from the approach disclosed herein. For instance, the computational model 32 can be implemented as a light-driven pump model, some examples including halorhodopsin (NpHR) and variant generations thereof, bacteriorhodopsin (BR), and archaerhodopsin-3 (Acrch) to name a few. Additionally, the computation model can be configured according to an opsin fusion (e.g., fusion between a channelrhodopsin and bacteriorhodopsin or halorhodopsin or others). When other opsins are modeled, the light source model 28 further will be configured to provide energy used to activate the cellular protein at the wavelength and energy requirements for driving such opsin, be it an ion channel, an ion pump (e.g., chloride pumps or proton pumps) or a fusion thereof.

In the example of FIG. 2, ChR2 is modeled as having three states including a closed state, an open state and a desensitized state. The ChR2 channel can transition from the closed state to the open state in response to excitation by a photon (e.g., having a blue wavelength of about 470 nm). The channel decays from the open state to the desensitized state according to a desensitization constant rate demonstrated as $G_D$. From the desensitized state, the channel returns to the closed state with a recovery constant demonstrated at $G_R$.

By way of further example, the instantaneous rate of change of these states for ChR2 can be defined in the model 32 by a set of two rate equations:

$$\frac{dO}{dt} = \varepsilon F_{ret} C - G_d O$$

$$\frac{dD}{dt} = G_d O - G_r D$$

where

O, C and D represent the number of ChR2 molecules in the respective states: open, closed, decaying;

$\varepsilon$ and $F_{ret}$ represent respectively the quantum efficiency and number of photons which strike the retinal molecules per second (e.g., flux ($\phi$), which can be computed as disclosed below);

$G_d$ and $G_r$ represent respectively the rates of channel closure and the recovery of photosensitivity, with $G_d = 1/t_d$ and $G_r = 1/t_r$.

The extracellular light source model 28 can be defined for any number of one or more light sources with parameters corresponding to the light source distribution, geometric spread of unfocused light, scattering and the absorbance of light by the tissue.

Figure 3:
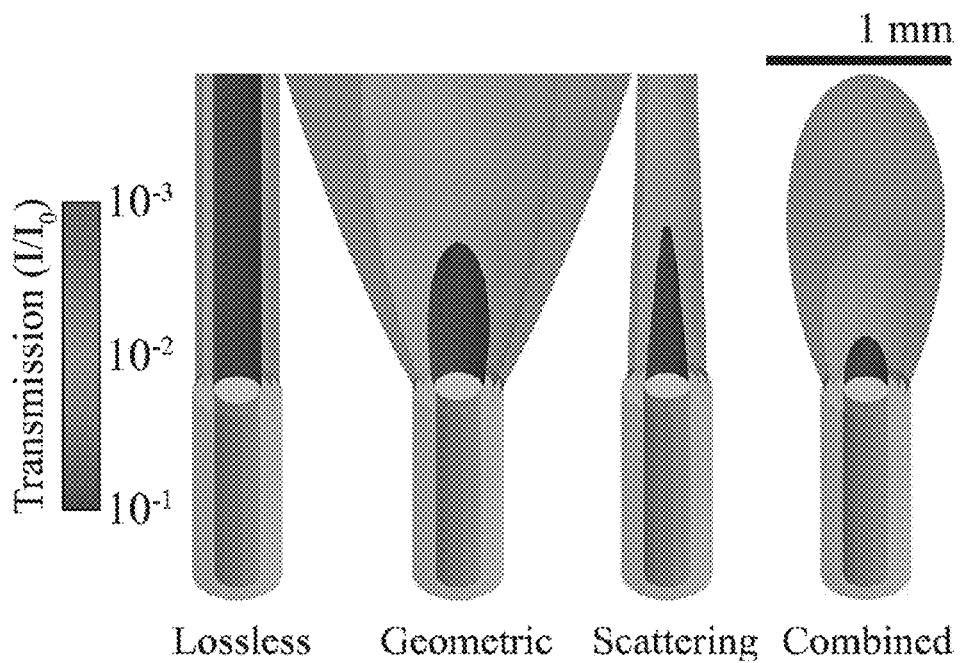
FIG. 3 depicts examples of different light source models.

FIG. 3 demonstrates an example of a three-dimensional representation for optical fiber light source models that can be implemented (e.g., corresponding to the light source model 28 of FIG. 1). FIG. 3 demonstrates graphical representations of different independent models of light distribution as well as a model representing a combination of geometric and scattering distributions. For the example of a optical fiber light source (e.g., as shown in the example models of FIG. 3), the light at each point can be defined by the source of light radiance and the transmittance of light between that point and the source as follows:

$$I(r,z)=T(r,z)I_0$$

where r is the radial distance and z is the height in the cylindrical coordinate system with the origin defined at the center of the optical fiber output.

The transmittance is wavelength dependent and can be broken down into corresponding linear components as follows:

$$T(r,z)=G(r,z)C(z)M(r,z)$$

where G describes the Gaussian distribution of light emitted by optical fibers,
C describes the conical spreading of unfocused light and
M describes the scattering and absorbance of light, such as according to the Kubelka-Munk theory of light propagation.

Examples of light model parameters that can be utilized for the extracellular light source model 28 during optical stimulation are demonstrated in the following Table 1.

|  | Description | Value |
|---|---|---|
| Optical fiber properties | | |
| $R_0$ | Optical fiber radius | 0.1 mm |
| z | Distance | 1 mm |
| $NA_{fib}$ | Optical fiber numerical aperture | 0.37 |
| pw | Illumination duration | 5 ms |
| Cell and tissue properties | | |
| K* | Absorbance coefficient | 7.37 mm$^{-1}$ |
| S* | Scattering coefficient | 0.125 mm$^{-1}$ |
| $n_{tis}$ | Tissue index of refraction | 1.36 |
| $\rho ChR2$ | ChR density** | $1.3 \times 10^{10}$ cm$^{-2}$ |

*Fit to data using least squares method.
**Channelrhodopsin-2 density assumed to be similar to that of bacteriorhodopsin estimated in *Xenopus* oocytes.

Additionally, for the example of extracellular light source model 28 for an optical fiber, light emitted from the optical fiber spreads as a cone of light with a divergence half-angle ($\theta_{div}$) dependent on the tissue index of refraction ($n_{tis}$) and the numerical aperture of the optical fiber ($NA_{fo}$):

$$\theta_{div} = \sin^{-1}\left(\frac{NA_{fo}}{n_{tis}}\right)$$

The radius of the light cone (R) at height z emitted by an optical fiber with radius $R_0$ spreads according to:

$$R(z)=R_0+z\tan(\theta_{div})$$

As the light diverges, the irradiance decreases according to the law of conservation of energy. Therefore, when considering the effects of geometry independently, the radiant power (P) is constant at all distances, and is equal to the irradiance (I) times the surface area illuminated:

$$P=I(z)\pi R(z)^2=I_0\pi R_0^2$$

where I is the irradiance at distance z from the optical fiber.

Therefore, the transmittance due to geometrical spreading (C) can be expressed as follows:

$$C(z) = \left(\frac{R_0}{R(z)}\right)^2$$

The Gaussian distribution of light (G) emitted by an optical fiber can be approximated as a transmittance:

$$G(r, z) = \frac{1}{\sqrt{2\pi}} \exp\left(-2\left(\frac{r}{R(z)}\right)^2\right)$$

According to the above equation, about 95.4% (2σ) of light is emitted by the core of the optical fiber, with the remaining about 4.6% emitted by the cladding. An example of Gaussian light distribution with and without geometrical spread is shown in FIG. 3.

Two additional factors affecting the light distribution are the scattering and absorptive properties of tissue, which factors can be implemented in the extracellular light source model 28 the neuron model 30 or be distributed between such models. To capture these effects, the model can employ the Kubelka-Munk general model of light propagation in diffuse scattering media. The Kubelka-Munk model to light diffusion provides an approximation of the transport equation. The transmittance of light in absorptive, scattering media (M) was:

$$M(r, z) = \frac{b}{a\sinh(bS\sqrt{r^2+z^2}) + b\cosh(bS\sqrt{r^2+z^2})}$$

where:
a=1+K/S
b=$\sqrt{a^2-1}$
S is the scatter coefficient per unit thickness (mm$_{-1}$),
K is the absorption coefficient per unit thickness (mm$^{-1}$).
This example model assumes that the sample is planar, optically homogenous, and illuminated normal to the sample surface with diffuse monochromatic light. Reflection and absorption processes further may be assumed constant over the illuminated area, and occur at infinitesimal distances. The coefficients for scattering (e.g., S=7.37 mm$_{-1}$, 95% CI 6.68-8.06) and for absorbance (e.g., 0.125 mm$_{-1}$, 95% CI 0.05-0.20) can be fit to light transmission data acquired from imaging data for the patient (e.g., geometry data 34 in FIG. 1).

Once the irradiance of light has been determined at each point along the neuron via the extracellular light source model 28, the flux of photons across each retinal molecule can be determined by the estimation method 14 to calculate a rate of ChR2 openings (e.g., changing from the closed to open state—see FIG. 2 and its corresponding description). The flux of photons across a single retinal molecule can be estimated by the energy content of the irradiated light. The energy of a single photon ($E_{photon}$) is determined by the Planck relation:

$$E_{photon} = \frac{hc}{\lambda}$$

where h ($6.63 \times 10^{-34}$ m²·kg/s) is Planck's constant, c is the speed of light ($2.998 \times 10^8$ m/s), and λ is the wavelength (e.g., 473 nm for C).

The energy of each photon is therefore $4.2 \times 10^{-19}$ J. The flux of photons (φ) can be determined by the law of conservation of energy:

$$\Phi = \frac{I(r,z)\sigma_{ret}}{E_{photon}}$$

where $\sigma_{ret}$ is the cross-section of a single retinal molecule (~$1.2\,e^{-20}$ m$^{-2}$).

The flux of photons (φ) across a single retinal molecule can further be used by the rate equations (e.g., as Fret above and as rate constants $K_{a1}$ and $K_{a2}$ below) disclosed herein to describe the rate of channel opening.

Figure 4:
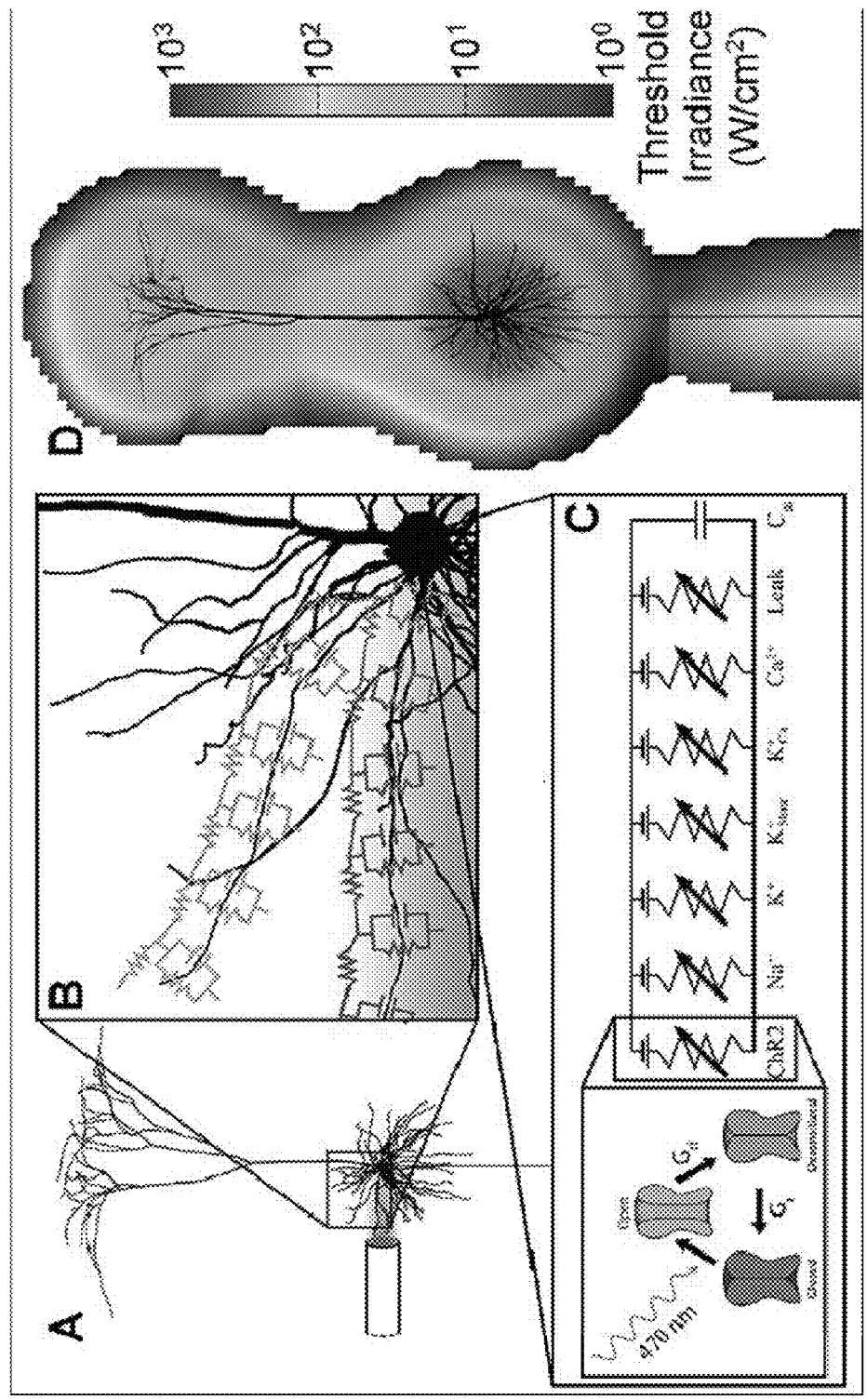
FIG. 4 depicts an example of a light neuron model.

With the ion channel model 32 embedded within the neuron model 30, the corresponding light neuron model 26 can be utilized to determine optical parameters via the VTDI evaluation method 16 to provide a corresponding estimate of the spread of optical stimulation. FIG. 4 depicts an example of a graphical representation of a light neuron model that can be implemented in the analysis and planning tool 12 of FIG. 1.

In the example of FIG. 4, the light neuron model includes a representation of the optical fiber light source illuminating a layer V pyramidal neuron demonstrated at (A). A corresponding neuron is represented by a multi-compartment cable model at (B). A transmembrane representation of the soma-dendritic compartments of the neuron model (e.g., Hodgkin-Huxlay type membrane dynamics) is also demonstrated at (C). A threshold irradiance contour plot (e.g., 10 μm step size resolution) is demonstrated at (D) in FIG. 4. In the contour plot (D), color (or grayscale) represents light irradiance (W/cm2) required to generate a propagating action potential and a pulse width (e.g., about 5 ms). Threshold for action potential generation in this example was calculated with the optical fiber positioned in a plane parallel to the long axis of the neuron, 500 μm above the neuron.

As explained above with respect to the example of mode of FIG. 2, in the light-neuron model 26, the closed, ground state for a ChR2 channel can be excited by photon inducement to the corresponding open and conducting state to provide corresponding action potential through the cells. The channel further decays to the closed desensitized state with a rate constant $G_D$ and recovers to the closed ground state with a further rate constant $G_R$ as mentioned above. In order to control the amount of stimulation for creating a propagating action and potential, the optical light source (e.g., an optical fiber) parameters can be determined from the light neuron model through the optimization process 18.

FIG. 4 further illustrates a threshold of radiance contour plot where the color represents light radiance W/cm² that is required to generate the corresponding action potential. The parameters associated with the source model in the parameterization space 20 can include pulse width as well as the geometric orientation of the optical fiber that is positioned relative to the neurons. Other types of light source models can be utilized such as those shown and disclosed in Zorzos, et al entitled *Multi Wave Guide Implantable Probe for Light Delivery to Sets of Distributed Brain Targets*, Dec. 15, 2010, Vol. 35, No. 24 in Optics Letters.

Figure 5:
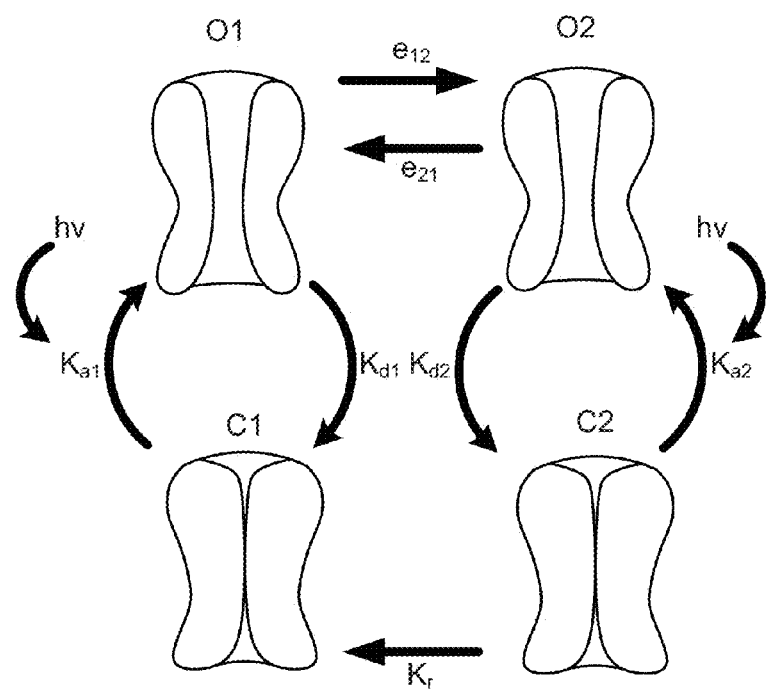
FIG. 5 depicts another example of a state diagram model of an ion channel responsive to illumination.

FIG. 5 depicts another example of a model (e.g., corresponding to the ion channel model 32 of FIG. 1) demonstrating channelrhodopsin-2 modeled as a nonspecific ion channel with four states: two closed states (C1, C2), and two open, conducting states (O1, O2). The channelrhodopsin-2 model can be inserted into the neuron model (e.g., model 30) uniformly or in a selectively distributed manner. In this example model, ChR2 can be excited from a closed, ground state (C1) to an open state (O1) secondary to absorption of a photon of approximately 470 nm light. This process can occur with a rate constant $K_{a1}$. ChR2 in the excited state (O1) can decay back to a closed state (C1, rate constant $K_{d1}$) or transition to a second excited state (O2, rate constant $e_{12}$). ChR2 in this second excited state is more stable, but has a lower ion conductance. ChR2 in state O2 can either return to the first open state (O1, rate constant $e_{21}$), or decay to a closed state (C2, rate constant $K_{d2}$). Finally, channels in state C2 can either be photoexcited back to O2 (rate constant $K_{a2}$), or be slowly converted thermally to C1 (rate constant $K_r$). The instantaneous rate of change of these states can be defined by a set of rate equations, such as follows:

$$\frac{dO1}{dt} = K_{a1}C1 - (K_{d1} + e_{12})O1 + e_{21}O2$$

$$\frac{dO2}{dt} = K_{a2}C2 + e_{12}O1 - (K_{d2} + e_{21})O2$$

$$\frac{dC2}{dt} = K_{d2}O2 - (K_{a2} + K_r)C2$$

$$1 = O1 + O2 + C1 + C2$$

In these equations, O1, O2, C1 and C2 represent the fraction of ChR2 molecules in the respective states. Examples for the fixed rate constants that can be utilized for this example four-state model are summarized in the following Table 2.

TABLE 2

OPTICAL STIMULATION MODEL

| | Description | Value |
|---|---|---|
| Channelrhodopsin-2 properties | | |
| $K_{d1}$ | Decay rate | 130 s$^{-1}$ |
| $K_{d2}$ | Decay rate | 25 s$^{-1}$ |
| $\Lambda_1$ | Decay factor | 30 μs |
| $\Lambda_2$ | Decay factor | 150 Ms |
| $e_{12}$ | Transition rate: light | 53 s$^{-1}$ |
| | Transition rate: dark | 22 s$^{-1}$ |
| $e_{21}$ | Transition rate: light | 23 s$^{-1}$ |
| | Transition rate: dark | 11 s$^{-1}$ |
| $K_r$ | Recovery rate | 0.4 s$^{-1}$ |
| $g_1$ | O1 state conductivity | 50 fS |
| $g_2$ | O2 state conductivity | 2.5 fS |
| $\sigma_{ret}$ | Retinal cross section | $1.2 \times 10^{-8}$ μm$^2$ |
| ε | Quantum efficiency | 0.5 |
| T | ChR2 time constant | 1.3 ms |
| $\rho_{ChR2}$* | ChR2 density | 130 μm$^{-2}$ |
| Fiber-optic properties | | |
| $R_0$ | Optical fiber radius | 0.1 mm |
| Z | Distance | 1 mm |
| $NA_{fib}$ | Optical fiber numerical aperture | 0.37 |
| Pw | Illumination duration | 5 ms |
| Tissue properties | | |
| K** | Absorbance coefficient | 7.37 mm−1 |
| S** | Scattering coefficient | 0.125 mm−1 |
| $n_{tis}$ | Tissue index of refraction | 1.36 |

TABLE 2-continued

OPTICAL STIMULATION MODEL

| | Description | Value |
|---|---|---|
| Cell properties | | |
| $r_m$ | Membrane resistivity | 30 k$\Omega$ cm$^2$ |
| $c_m$ | Membrane capacitance | 0.75 µF cm−2 |
| $r_i$ | Axial resistivity | 150 $\Omega$ cm |
| $V_m$ | Rest Membrane potential | −70 mV |

*Channelrhodopsin-2 (ChR2) density assumed to be similar to that of bacteriorhodopsin measured in *Xenopus* oocytes.
**Fit to data using least squares method. O1 and O2, open states.

The activation rate constants $K_{a1}$ and $K_{a2}$ are dynamic parameters that depend upon the light irradiance, which can also vary in the computation. Accordingly, parameters $K_{a1}$ and $K_{a2}$ can be calculated dynamically, such as according to the following.

$$K_{a1} = \begin{cases} \varepsilon_1 \Phi(1 - e^{-t/\tau}), & \Phi > 0 \\ \varepsilon_1 \Phi_0(e^{-(t-t_0)/\tau} - e^{-t/\tau}), & \Phi = 0 \end{cases}$$

$$K_{a2} = \begin{cases} \varepsilon_2 \Phi(1 - e^{-t/\tau}), & \Phi > 0 \\ \varepsilon_2 \Phi_0(e^{-(t-t_0)/\tau} - e^{-t/\tau}), & \Phi = 0 \end{cases}$$

where:
$\varepsilon_1$ and $\varepsilon_2$ are the quantum efficiency of photons which attempt to excite channelrhodopsin from a closed state to the corresponding open state;
$\phi$ is the photon flux per unit area during illumination;
$\phi_0$ is equal to $\phi$ during prior illumination (dark phase);
t is the time since prior illumination began;
$t_0$ is the time since prior illumination ended (dark phase); and
$\tau$ is the time constant of channelrhodopsin, shown in Table 2.

Determination of the ChR2 transmembrane channel conductance depends on the transmembrane voltage ($V_m$), the reversal potential ($E_{cat}$, set to 0 mV), and the channel conductance ($g_{ChR2}$). The ChR2 current during illumination ($i_{max}$) is determined by Ohm's law:

$$i_{max} = (V_m - E_{cat}) g_{ChR2}.$$

ChR2 channel conductance is dependent on the state of the channel, with zero conductance in states C1 and C2, low conductance ($g_2$) in state O2, and high conductance ($g_1$) in state O1 (See Table 2).

After a period of illumination, the ChR2 transmembrane current decays exponentially. This decay has been fit experimentally by separating the current into a fast ($i_{fast}$) and a slow component ($i_{slow}$). The ChR2 transmembrane current, post-illumination, can thus be defined as:

$$i = i_{slow} e^{-\Lambda_1(t-t_0)} + i_{fast} e^{-\Lambda_2(t-t_0)}$$

where $\Lambda_1$ and $\Lambda_2$ are current decay factors. As time increases, the net transmembrane current decays to zero. The fast and slow components of the current are defined by:

$$i_{fast} = i_{max} \frac{O1_0(K_{d1} + (1-\gamma)e_{12,dark} - \Lambda_1) + O2_0(\gamma(K_{d2} - \Lambda_1) - (1-\gamma)e_{21,dark})}{\Lambda_2 - \Lambda_1}$$

$$i_{slow} = i_{max} \frac{O1_0(\Lambda_2 - K_{d1} - (1-\gamma)e_{12,dark}) + O2_0((1-\gamma)e_{21,dark} + \gamma(\Lambda_2 - K_{d2}))}{\Lambda_2 - \Lambda_1}$$

where $O1_0$ and $O2_0$ are the fraction of open channels during the prior illumination phase, and $\gamma$ is the ratio of the conductance of the two states O2 and O1 ($\gamma = g_2/g_1$).

As part of the light-neuron model, in some examples, the ChR2 model can be inserted in all compartments of the neuron model, with a uniform ChR2 channel density of 130 µm$^{-2}$. In other examples, to simulate the effect of non-uniform distributions, ChR2 can be distributed either in specific compartments (see, e.g., Table 3), or by distributing its density based on distance from the soma (see, e.g., FIG. 6). Distance-based ChR2 distribution can be performed by weighting the channel density by the path distance from the center of the soma to each point on the dendritic arbor, and scaling the density such that the total number of the channels in the soma-dendritic arbor remained constant. For the apical distribution, the most distant compartment has the maximal density, while the soma had minimal density of ChR2. For the basal distribution, the distribution can be reversed.

TABLE 3

| ChR2$^+$ Compartment(s) | Threshold, mW/mm$^2$ | $1_{ChR2}$, nA | No. Open ChR2 |
|---|---|---|---|
| Soma | 14,511 | 1.11 | 176,945 |
| Dendrite | 205 | 1.72 | 247,975 |
| Soma + dendrite | 197 | 1.72 | 247,259 |
| Soma + dendrite + axon | 190 | 1.71 | 243,283 |
| Axon | 2,104 | 0.33 | 42,386 |

$1_{ChR2}$ total current through all ChR2.

Figure 6:
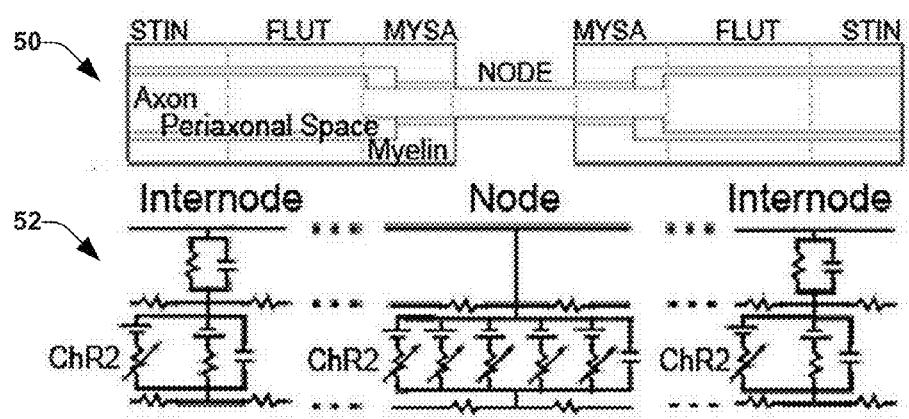
FIG. 6 depicts an example of a myelinated axon model with ChR2 inserted into compartments thereof.

FIG. 6 depicts an example of a myelinated axon model with ChR2 inserted into compartments thereof. The axon model can correspond to the McIntyre-Richardson-Grill (MRG) model of myelinated mammalian axon. In a first part 50, FIG. 6 shows an example diagram of the various nodal and internodal compartments. For instance, extracellular compartments can include three different parts: myelin attachment segments, paranode main segments and internode segments (MYSA, FLUT and STIN). In the lower part, FIG. 6 demonstrates an example of a circuit diagram 52 including additions of ChR2 channels inserted into the axon membrane.

For example, the model can be implemented where the Node and FLUT regions of the MRG model contained half the density of ChR2 compared to the STIN and MYSA regions. In other examples, different densities of ChR2 could be utilized, which may be uniform or non-uniformly distributed across the different regions. Unless specified otherwise, it should be noted that when ChR2 density is stated in the text it refers to the STIN ChR2 density, as this section of the axon constitutes the vast majority of the total axonal membrane surface area. Interestingly, increasing the node and paranode ChR2 density to obtain a uniform distribution across all axonal compartments does not significantly change the threshold irradiance respective to axon diameter.

Figure 7:
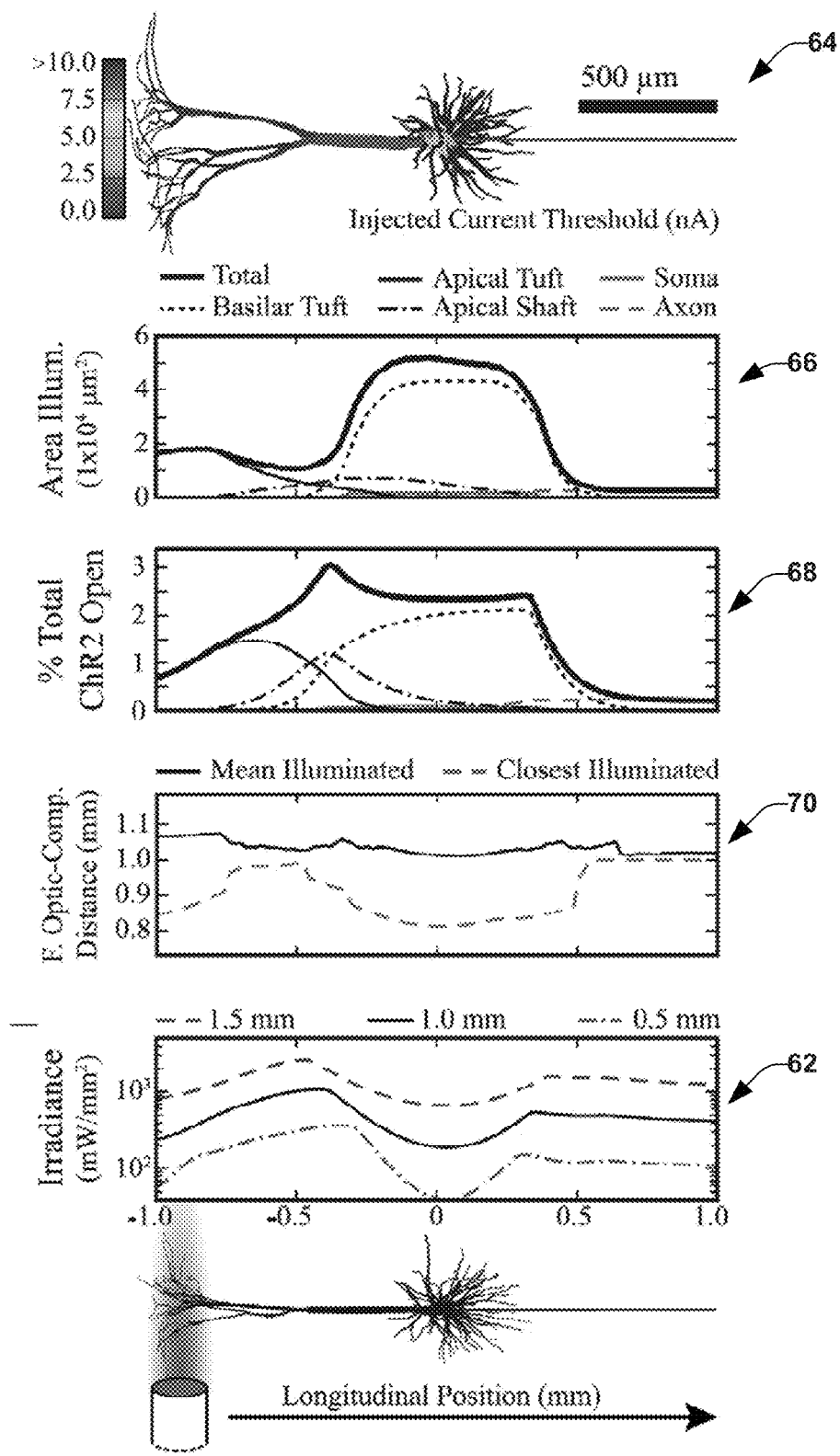
FIG. 7 depicts plots characterizing an example optical stimulation profile over various parameters.

The light-neuron model further can compute the threshold for activation depending on the orientation and distance of the light source relative to the neuron. FIG. 7 depicts characteristics of an example optical stimulation profile which demonstrate that the threshold for activation is dependent on the fiber optic-neuron orientation. As shown at 62, the illumination threshold can be determined for a range of fiber optic locations along the neuron (e.g., from a distance of 500, 1000 and 1500 μm) with light directed perpendicular to the long axis of the neuron. The plot 62 thus demonstrates threshold irradiance level (±0.1%) that is required to generate a propagating action potential from different fiber-optic-to-neuron distances.

The threshold profile in this example is nonlinear, being influenced by many factors. In FIG. 7, the plot 64 shows a spectrum of current injection thresholds at each individual model compartment required to generate an action potential in a non-illuminated neuron. The contribution of depolarization in each given compartment can contribute to the generation of an action potential. Additionally or alternatively, as demonstrated at 66, the membrane area that is illuminated can contribute to the generation of an action potential. The number of channels opened due to the flux of photons across the membrane, as shown at 68, can also contribute to the generation of an action potential. The plot 68 demonstrates the percent of total ChR2 channels in the open state at the end of a threshold stimulation pulse. The distance between the fiber optic and neuron compartments, demonstrated in plot 70, is yet another parameter that can influence the generation of an action potential. Plot 70 demonstrates that distance from the output end of the fiber optic to either the closest illuminated neuron compartment or the average position of all illuminated compartments.

From FIG. 7, it can be shown that the activation threshold is lower near the cell body and the apical dendrites, and higher along the apical shaft and axon. This general relationship exists at larger fiber-optic-to-neuron distances. During stimulation of the somatic/basal region, action potentials tend to initiate in the axon initial segment. As stimulation moves laterally along the apical shaft and into the apical tuft, the site of action potential initiation moves and localizes to the apical dendrites.

The ChR2 model parameters further can be configured to account for additional region of minimal irradiance threshold in the apical tuft region. At close distances (100 μm), there is some degree of additional spatial dependence, particularly among the apical dendrites, though to a lesser extent than would be possible with focused light.

Figure 8:
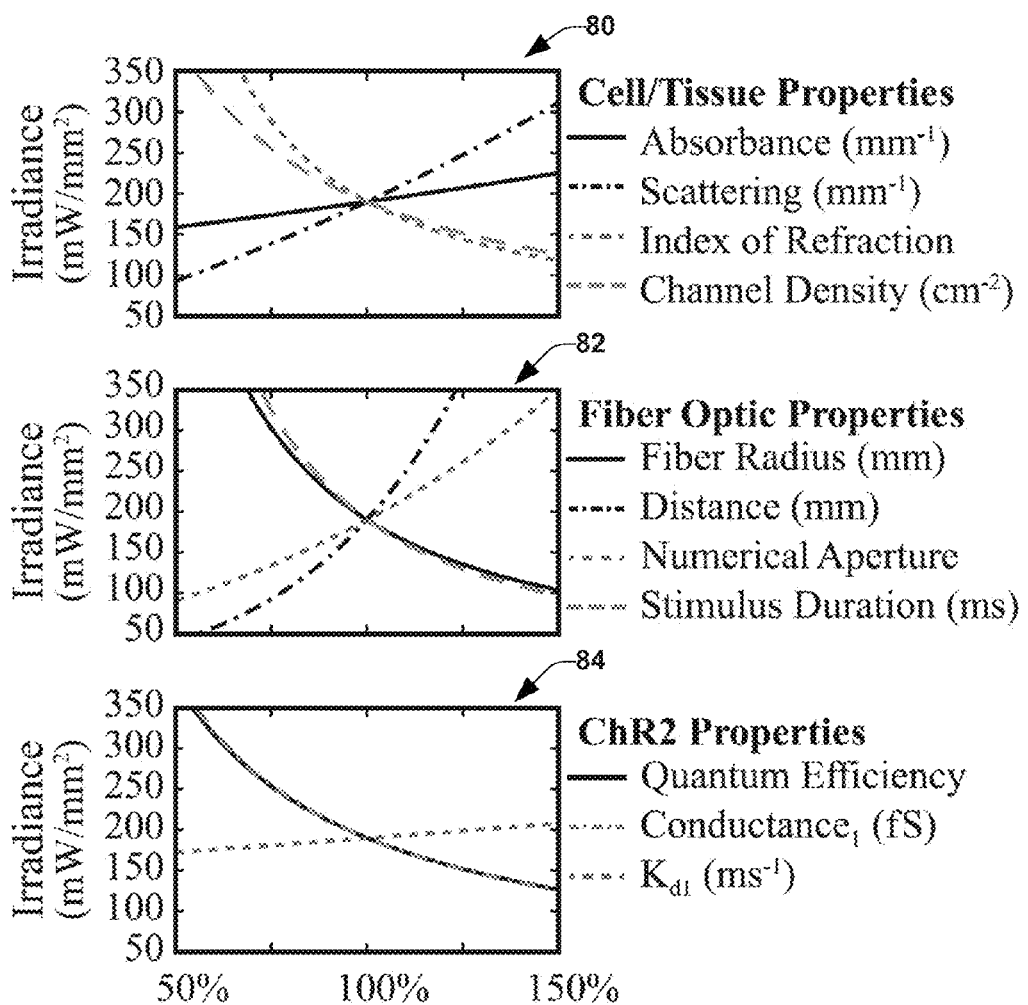
FIG. 8 depicts plots demonstrating sensitivity of the ion channel model to various parameters.

FIG. 8 includes plots 80, 82 and 84 demonstrating sensitivity of the ion channel model to various parameters. In the example plots of FIG. 8, each model parameter was varied independently (±50%), and the threshold irradiance level necessary to generate an action potential was determined (±0.1%). Default values are listed in Table 2, although these values can be varied, in response to a user input, depending on application requirements since the results of optogenetic neural stimulation can be sensitive to several parameters. As demonstrated in the plot 80, for example, a 50% increase in the ChR2 channel density can result in a decreased irradiance threshold from about 190 mW/mm$^2$ to about 126 mW/mm$^2$ for a given default fiber-optic-neuron orientation. As a further example, positive correlation is shown at 80 seen in the absorption/scattering coefficients of brain tissue, fiber-optic-to-neuron distance, numerical aperture of the fiber optic, and the rate of channel desensitization ($K_{d1}$). A decrease in any of these parameters resulted in a lower stimulus threshold. Negative correlation was seen in the tissue index of refraction, ChR2 channel density, fiber optic radius, stimulus duration, single channel conductance and quantum efficiency. An increase in any of these parameters would result in a lower stimulus threshold. Other parameters that had no effect on stimulus thresholds were not shown, which include $K_{d2}$ and $K_r$; rather than influencing the stimulus threshold, these two parameters affect plateau currents, as well as channel conductance post-illumination. Therefore, it should be noted that these parameters could play a more important role in repetitive stimulation analyses. The effects of varying other cell/tissue parameters are shown at 80.

Plots 82 and 84 demonstrate affects on irradiance in response to varying fiber optic properties and ChR2 properties, respectively. Each of these parameters (e.g., corresponding to parameters 20 of FIG. 1) in the light neuron model can be adjusted individually or in part for identifying optimal parameters for achieving a desired VTDI, as disclosed herein.

Results from the fiber-optic radius parameter manipulation may be potentially counterintuitive. For example, increasing fiber-optic radius from 0.2 mm to 0.3 mm decreases the irradiance threshold from 190 mW/mm$^2$ to 104 mW/mm$^2$; however, it also increases the surface area of the fiber optic, with a net increase in the radiant power. Instead, decreasing the fiber-optic radius to 0.1 mm is predicted to decrease the radiant power requirement to 4.74 mW. For all other parameters in FIG. 8, radiant power is proportional to irradiance.

Figure 9:
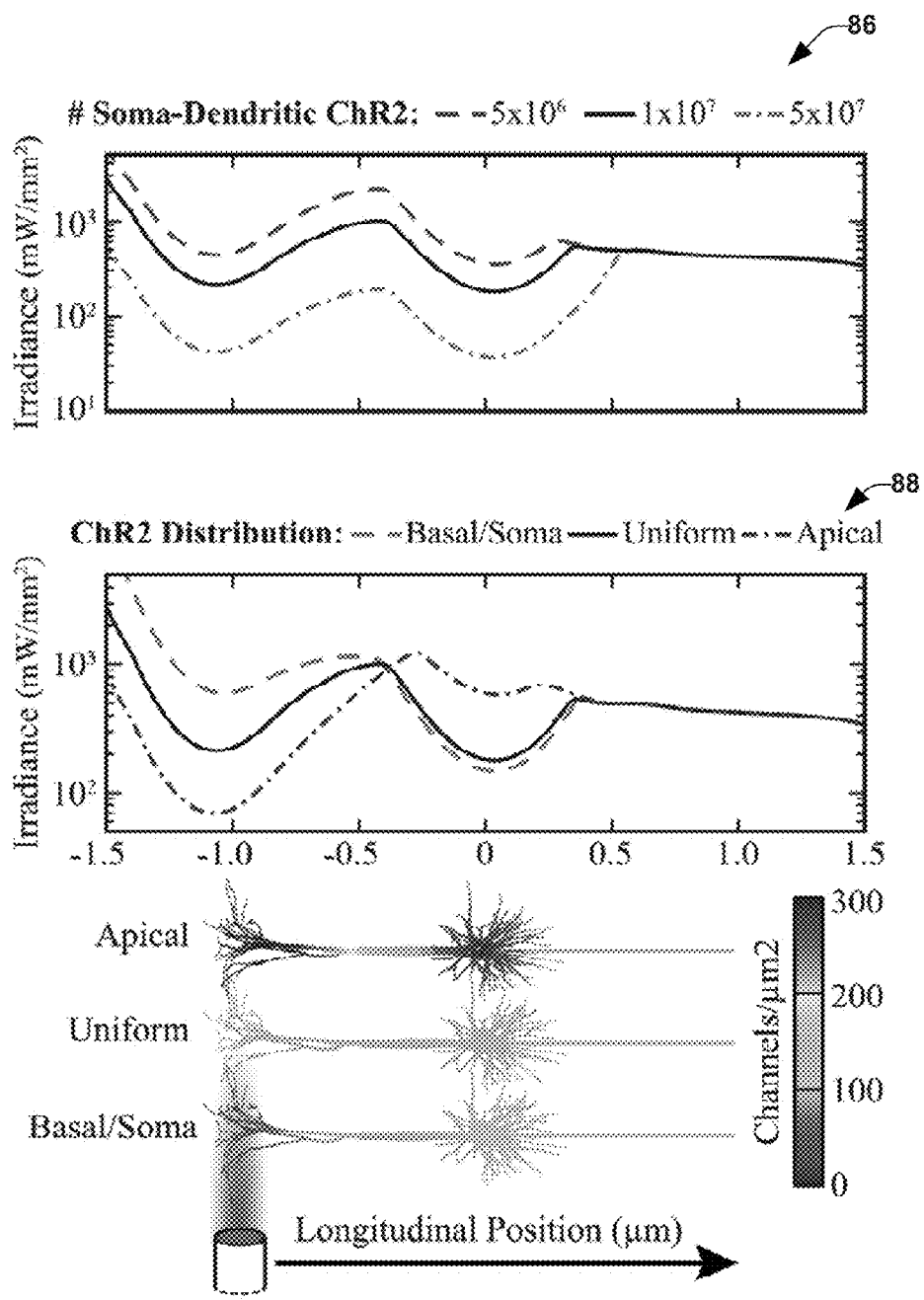
FIG. 9 depicts plots demonstrating irradiance for uniform and non-uniform ChR2 densities.

In some of the examples disclosed herein ChR2 expression can be parameterized in the computation model (e.g., model 26 of FIG. 1) as being uniformly distributed (e.g., in the soma-dendritic compartments) and constant. In other examples, such as shown in FIG. 9, ChR2 expression can be implemented as variable (e.g., non-uniform) distribution. As mentioned above, the ChR2 distribution and overall channel density can have a large impact on the stimulus threshold (see e.g., FIG. 8). For the example of FIG. 9, it is assumed that the threshold irradiance required to generate an action potential was calculated by the model with the fiber optic oriented perpendicular to long axis of the neuron. Plot 86 demonstrates stimulation profiles of a neuron with 5, 10 or 50 million channels distributed uniformly in the soma-dendritic compartments of the model. For each of the curves computed, ChR2 expression in the axon was set uniform and constant at the default model value. Plot 88 depicts a stimulation profile with 3 different distributions of 10 million ChR2 channels across different compartments: (a) basal/soma with higher expression of ChR2 in the basal tuft and somatic compartments, (b) uniform with equal channel density across all compartments, and (c) apical with higher expression of ChR2 in the apical tuft. Plot 88 further demonstrates that higher densities of channels inserted in to compartments in the apical region led to lower thresholds in the apical region, at the cost of higher thresholds in the somatic/basal region. Higher somatic/basal distributions resulted in the opposite relationship.

Figure 10:
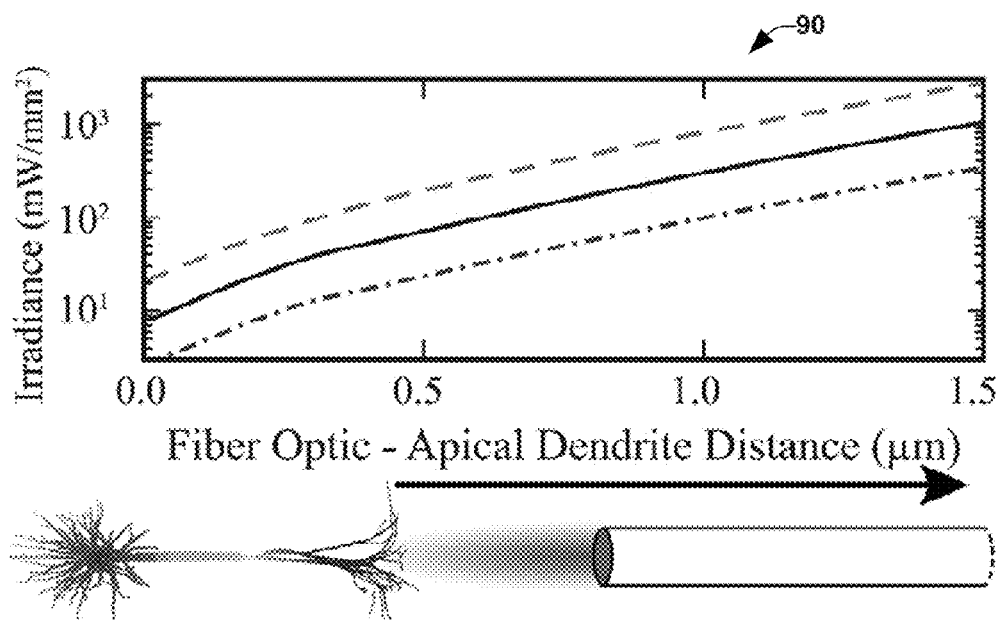
FIG. 10 depicts plots demonstrating irradiance as a function of apical-dendrite distance.

FIG. 10 demonstrates a plot 90 computed threshold irradiance for an example where an optical fiber optic is placed along the longitudinal axis of the neuron and directed at the apical tuft. The threshold irradiance was calculated as a function of the fiber optic distance from the apical tuft for the same three different ChR2 distributions used the plot 88 of FIG. 9. In the example of FIG. 10 for apical stimulation parallel to the long axis of the neuron (e.g. cortical stimulation perpendicular to the surface of the cortex), there are substantial decreases in the irradiance threshold with an apical distribution. For example, the 1 mm distance threshold of about 299 mW/mm$^2$ with a uniform distribution reduced to about 99 mW/mm$^2$ with an increased apical distribution as compared to a basal/soma distribution.

In view of the foregoing, the activation threshold is dependent on the biophysical parameters of ChR2, its distribution, the tissue properties, the characteristics of the fiber optic and its orientation with respect to the neuron. Thus, the parameters of the model 26 can be selectively controlled to determine a minimal optical power to achieve a desired target VTDI.

Additionally or alternatively, two other example computational models that can be implemented to represent the ChR2 density (channels/$cm_2$) as a function of axon diameter are Diameter Dependent Axonal Expression (DDAE) and Uniform Axonal Expression (UAE) models. DDAE assumes that ChR2 density in the axon is constant per membrane surface area. In this model, larger diameter axons express more ChR2 than smaller diameter axons. The Uniform Axonal Expression (UAE) model assumes that ChR2 expression is constant per unit length of the axon. This model results in an inverse relationship for ChR2 density per membrane surface area to axon diameter, proportional to $1/\pi D$.

Figure 11:
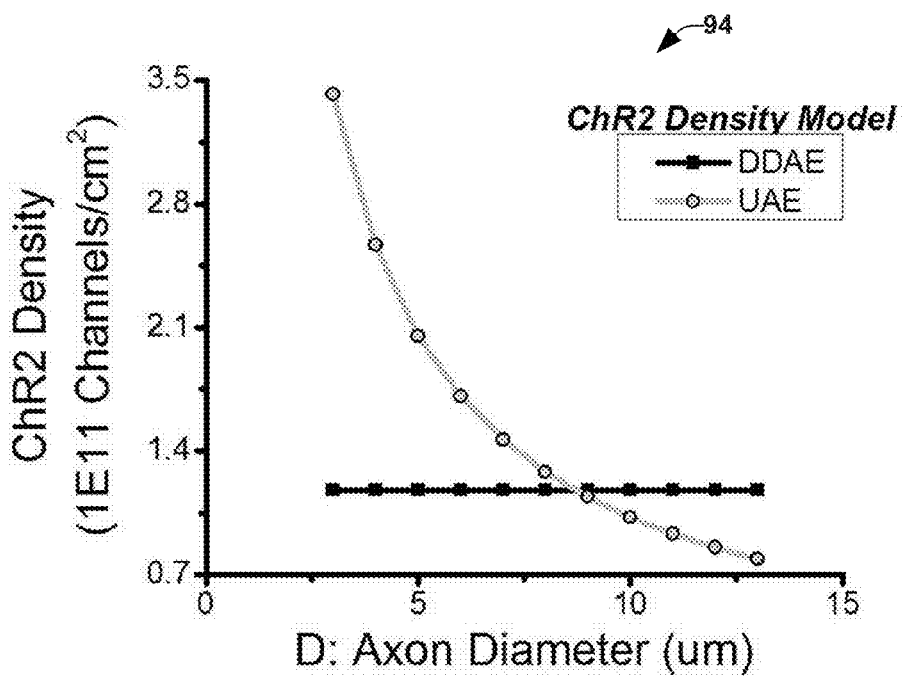
FIG. 11 depicts plots demonstrating ChR2 density as a function of axon diameter for different types of ion channel models.

To help illustrate properties parameterized by each of the UAE and DDAE models, FIG. 11 provides of plot of ChR2 density as a function of axon diameter. As shown in FIG. 11, the UAE model has an inverse ChR2 density per surface membrane area (channels/$cm^2$) relationship to axon diameter. The DDAE (Diameter Dependent Axonal Expression) model has a substantially constant ChR2 density per axonal surface membrane area (channels/$cm^2$). As disclosed herein, the UAE and DDAE models or variations thereof can be configured for use with other opsins, including other light-driven ion channel models and light-driven pump models.

Referring back to FIG. 1, the estimation method 14 thus can evaluate a corresponding VTDI via the VTDI evaluation method 16 for a given set of parameters 20 and target VTDI 22. The optimization method 18 further can be programmed to calculate a set of parameters for optical stimulation, including trajectory, light source placement, light source parameters (e.g., type of light source), intensity, light distribution and the like. The estimation and optimization may be repeated over the parameter space. For instance, the estimation and optimization may be programmed to repeatedly solve the light-neuron model over a plurality of model conditions to provide respective estimates of the VTDI. For example, during each iteration, one or more parameters can be varied, such light pulse duration parameters, source to neuron depth parameters, axon diameter parameters and microbial opsin model parameters, to name a few. As another example, the optimization can quantitatively independently vary a density of microbial opsin expression and associated ion channel conductivity to calculate parameters for the estimated VTDI. The respective estimates of VTDI can be compared with a target VTDI to ascertain threshold of irradiation, such as can be a threshold to initiate action potential or to inhibit the action potential. The resulting parameters can be stored in memory and provide a corresponding set of parameters that can be utilized to implement a desired spread of optical stimulation to achieve the target VTDI 22.

As a further example, the optimization algorithm 18 can be programmed to determine a set of optogenetic stimulation parameters 20 that collectively can be used to control stimulation to achieve the target VTDI 22. Those skilled in the art will understand and appreciate various optimization methods that can be utilized by the optimization algorithm 18 to solve the light-neuron computational model 26 to determine the structural parameters and/or the electrical parameters for approximating the target VTDI 22, which has been determined to achieve a desired therapeutic effect. The optimization algorithm, for instance, can determine the parameters by maximizing stimulation for the target VTDI with a minimum amount of energy, such as by computed the parameters to achieve a reduce irradiance threshold for the VTDI.

By way of example, the estimation 14 and optimization 18 can be performed pre-operatively or intra-operatively or it can be performed both pre-operatively and intra-operatively. The optimization 18 further may be extended over plural procedures to encompass delivery of the viral vector as well as positioning a light source and setting stimulation parameters. The fluid delivery part of the optimization can be implemented as disclosed in relation to FIG. 12 herein. The optimization algorithm 18 can also be implemented pre-operatively in relation to the optical stimulation part of the process. For instance, a customized light source design can be computed pre-operatively, which can be selected from a set of commercially available structures (e.g., optical fibers) or a fully customized patient-specific design can be generated based on an estimated volume of transfection. The optimization 18 can be programmed to determine the set of stimulation parameters to achieve the target VTDI 22 based on the geometry data 34, the volume of transfection (computed from the model 24), the light source configuration (computed from the light source model 28), location of the light source in the volume of transfection, such as in a stereotactic coordinate system for the patient.

By way of further example, volume based optimization 18 can be applied to the target VTDI 22 and employ the models 24-32 to compute optical stimulation parameter settings to achieve a desired therapeutic effect. The clinically defined therapeutic stimulation parameters thus can represent the gold standard. Quantitative measures as well as qualitative measures can be utilized as parameters to determine appropriate optimal settings to achieve the desired therapeutic results. The particular quantitative or qualitative parameters may vary according to the particular symptoms of the patient. For instance, known clinical rating scales can provide quantitative measures for a variety of conditions, including but not limited to bradykinesia, rigidity, tremor, and bimanual hand function.

The tool 12 can provide a corresponding output to a display 36 such as can include a graphical representation of patient anatomy, such as the brain or other parts of the nervous system. The display 36, for example, can be generated to include a graphical representation of patient anatomy based upon MRI imaging (e.g., corresponding to the geometry data 34). Other types of geometry data can also be utilized in conjunction with the analysis and planning tool 12 for generating the corresponding display, including actual images for a given patient or generic models corresponding to patient anatomy.

As an example, the display 36 can demonstrate a graphical representation, textual representation or a combination graphical and textual information associated with determining the spread of optical stimulation or associated parameters. As one example, a graphical interface can provide data to the display 36 for overlaying one or more selected estimated volumes over a display of the patient anatomy. The estimated volumes can include an estimated volume of infusion, volume of diffusion, as well as the estimated VTDI for computed optical stimulation parameter space. A representation of a target VTDI can also be generated and provided to the display 36. Such a representation provides a visual demonstration of expected performance based on corresponding optical stimulation parameters calculated according to a light-neuron model as disclosed herein.

The system 10 can also include a user interface 38 that can be utilized to set starting parameters utilized the estimation method 14. For instance, parameters of the model can be set to fixed or constant values, such as can be selected from a set of default values. Other parameters can be set to variable values, such as disclosed herein (e.g., parameters of the ion channel model 32), in response to a user input.

The user interface can also be utilized to control other aspects of the display, configure interfaces and enable user-interaction with the tool 12. For example, the user interface 38 can rotate the image provided in the display 36 in response to user input data. Alternatively in other portions, menus or other input mechanisms can be provided to input other patient data that may be relevant to the estimation performed at 14. A different assumption for a given model can also be modified for the respective models 24 and 26. Other parameters in the parameter space 20 can also be constrained in response to the input data received via the user interface 38. The user interface 38 can also be used to select what computed volumes are displayed on a graphical depiction of patient anatomy.

A user can also employ the user interface 38 to constrain the range of parameters 20 or another part of the procedure, the granularity of such parameters as well as to program other parameters being used in the procedure. The user interface 38 can also be utilized to interface and enable acquisition of data (e.g., geometry data 34) from an associated imaging device, such as a magnetic resonance imaging (MRI) system, a computer tomography (CT) system or other imaging modality.

Additionally, the system 10 can be utilized to data in a format to guide and/or control robotic navigation, control an infusion pump and/or drive a light source based on the design parameters determined to achieve a desired therapeutic effect for a given patient. For instance, the stimulation parameters being programmed to a stimulation device can vary depending on the light source configuration that has been selected for a given patient.

FIGS. 12A through 12D demonstrate an example of a type of output that can be represented in the display 36 of FIG. 1. In the example of FIG. 12A through 12D demonstrate parts of an optical stimulation process in the context of a mouse brain, with image contrast inverted to facilitate reproducibility in the context of a patent application. It is to be understood and appreciated that the systems and methods disclosed herein are not limited to a mouse or other type of animal brain or to the brain itself but can be utilized for implementing optogenetic stimulation of other tissue structures (e.g., peripheral nerves, spinal cord and the like), such as disclosed herein.

Figure 12A:
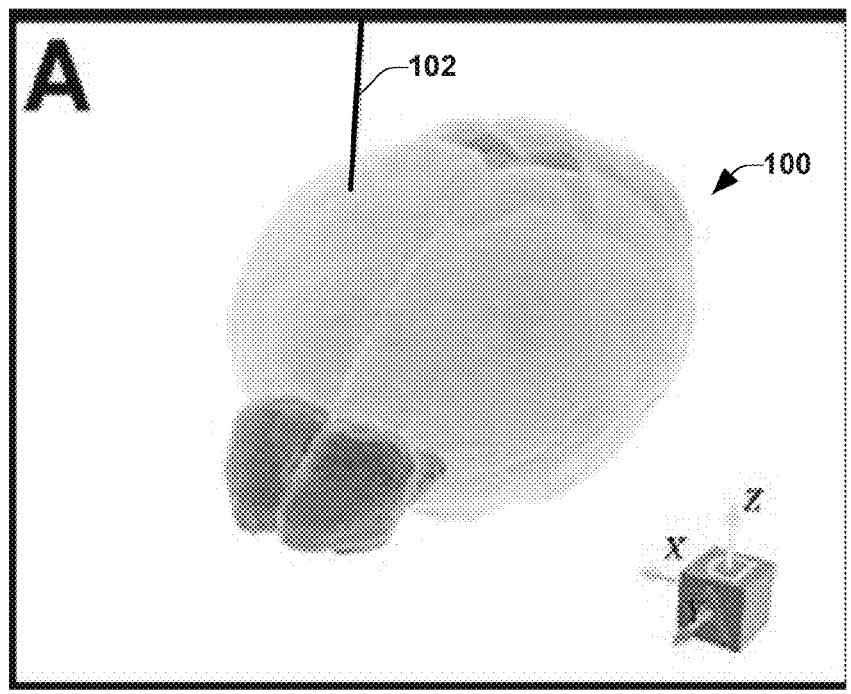
FIGS. 12A-12D depict examples of parts of an optogenetic stimulation process, including spread of stimulation model.
Figure 12B:
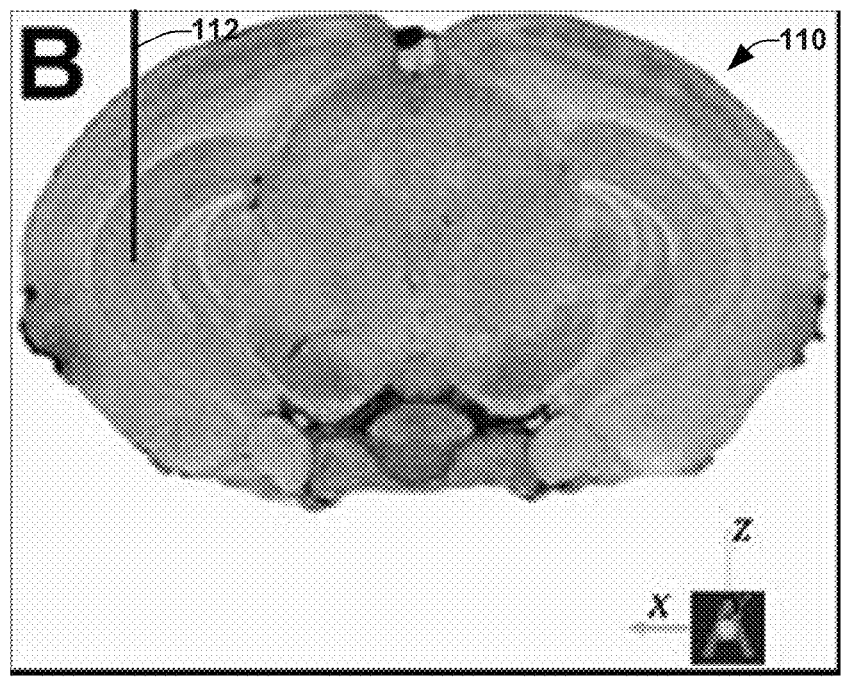
Figure 12C:
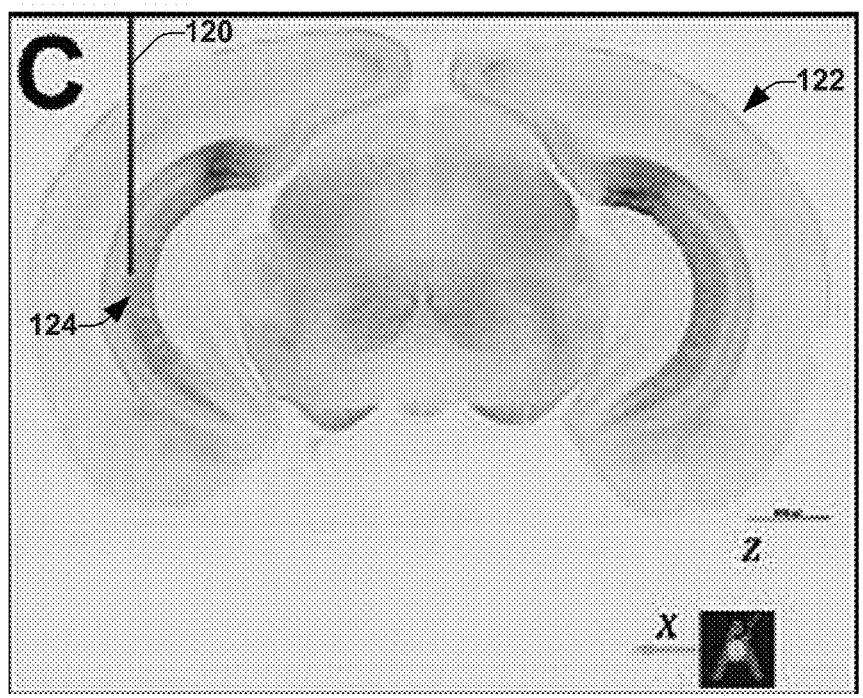
Figure 12D:
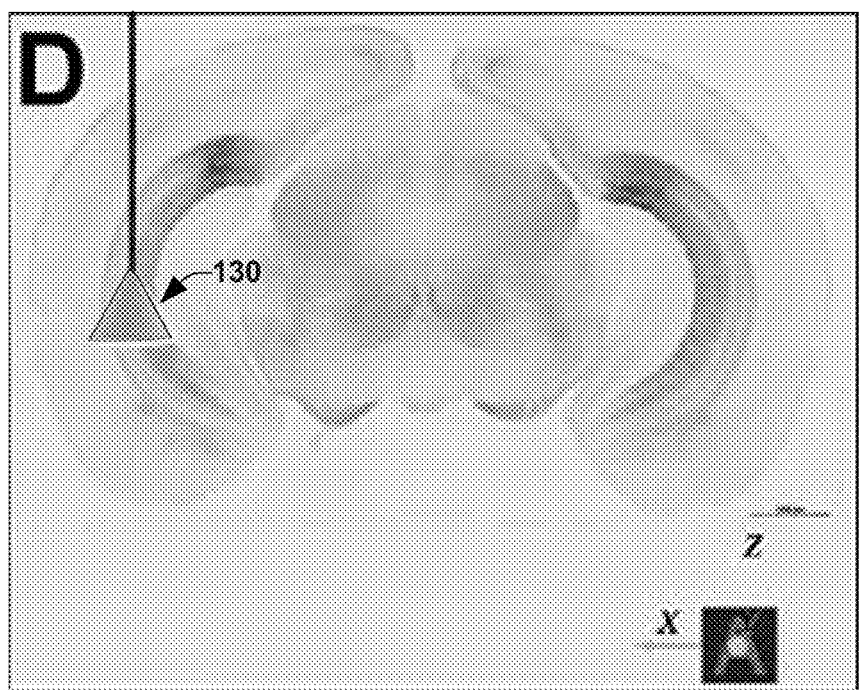

FIG. 12A depicts a 3-D representation of a mouse brain 100 with a light source (e.g., optical fiber) 102 implanted in a right hemisphere. FIG. 12B demonstrates a coronal slice from an atlas brain 110 with an optical fiber 112 implanted in the hippocampus. FIG. 12C demonstrates a graphical representation of a simulated optical fiber 120 co-registered with the coronal slice of the atlas brain and tissue 124 that has been transfected with ChR2, such as can be computed via a volume of transfection model as disclosed herein. In FIG. 12D, a graphical representation of a corresponding VTDI 130 is superimposed over a corresponding volume of transfection from which a corresponding spread of stimulation and action potentials can be ascertained, such as disclosed herein.

Figure 13:
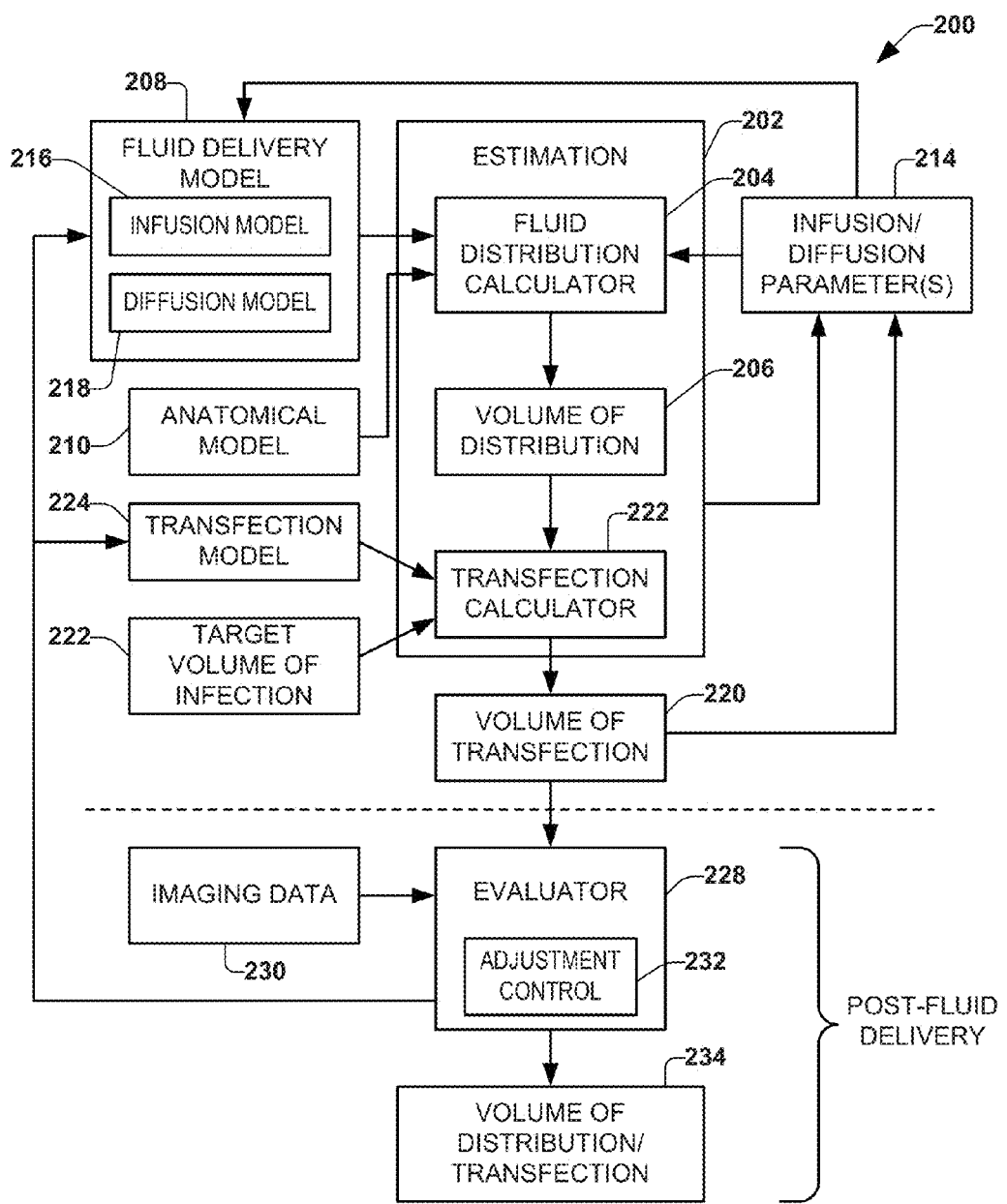
FIG. 13 depicts a functional block diagram of an example approach that can be employed to estimate a volume tissue infection.

FIG. 13 depicts an example of a system that can be utilized to ascertain a volume of transfection and volume of distribution for use in estimating spread of optical stimulation as shown and described herein. The system can be implemented as a computer-implemented method, such as based on instructions, executable by a processor, stored in a non-transitory machine-readable medium, such as volatile or non-volatile memory structures.

The system 200 includes an estimation method 202 that includes a fluid distribution calculator to calculate a corresponding volume of distribution for a vector solution that can be delivered into a target site of a patient. The fluid distribution calculator 204 computes the volume of distribution 206 based on a fluid delivery model 208 and an anatomical model 210 to achieve a corresponding target volume based on target volume data 212. The target volume data 212 can correspond to a target volume of distribution, a target volume of transfection or a combination of data corresponding to a data of volume distribution and volume of transfection. Thus, the fluid distribution calculator 204 can be programmed with instructions to optimize a set of delivery parameters in the parameter space 214 to achieve a target volume of distribution based on the target volume 212.

As an example, the fluid delivery model 208 can include an infusion model 216. The infusion model 216 can parameterize a fluid delivery mechanism (e.g., a catheter model), a trajectory for the delivery mechanism as well as include flow rate parameters (e.g., inflow rate, duration and backflow) and other related fluid dynamic parameters for the fluid or the delivery site. For example, the anatomical model 210 further constrains the infusion model and the calculations according to the density of tissue in the cellular and intercellular spaces. The fluid distribution calculator 204 can calculate a volume of infusion in response to delivering a quantity of solution based upon corresponding infusion parameters in the parameter space 214.

With a given volume of infusion, the fluid distribution calculator 204 further can calculate corresponding diffusion of the infused volume, such as according to a diffusion model 218. The diffusion model 218 can parameterize aspects of diffusion of the infused vector, which can vary according to the tissue hydraulic conductivity, pore fraction and the diffusion tensor for the corresponding molecule being infused. The fluid distribution calculator 204 can calculate a resulting volume of distribution corresponding to diffusion based on the diffusion model 218 following the initial infusion of vector solution. This can be calculated such that the volume of distribution 206 for diffusion substantially matches a target volume of diffusion (e.g., part of or computed from the target volume data 212). Alternatively or additionally, the volume of distribution for distribution, as calculated at 206, further can be employed to ascertain a volume of transfection 220.

For example, the estimation process 202 can also include a transfection calculator 222 that employs a transfection model 224 to estimate a volume of transfection based upon the resulting volume of distribution due to diffusion and infusion of the vector. The transfection model 224, for example, can be generated based upon experimental data that quantifies the expression of the selected protein for a given concentration of the vector virus that has been infused in selected tissue. The transfection model 224 further can be programmed to account for anatomical variations and tissue structure based on the anatomical model 210 and the estimated volume of distribution 206 in such tissue.

The transfection calculator 222 can further be implemented as part of the estimation process so that the volume of transfection 220 can substantially match a desired target volume of transfection such as provided by the target volume data 212. Based on the evaluation of the volume of transfection 220 relative to the target volume, the estimation process 202 can adjust one or more of the fluid delivery parameters in the parameter space 214. The corresponding process can be repeated to provide a volume of transfection that substantially matches the desired target volume. It will be appreciated that the volume of transfection may exceed the volume intended to be stimulated since optical stimulation parameters can be controlled to optically stimulate a smaller volume of cells for achieving the desired effect.

As also demonstrated in FIG. 13, an evaluator 228 can compare the estimated volume of transfection and estimated volume of distribution 206 relative to imaging data 230. By way of example, the viral vector can include a tag or markers that can be detected by a corresponding imaging modality. Accordingly, following infusion of the vector virus into the tissue, imaging can be performed to determine, for example, an actual volume of distribution for the viral vector. The volume of distribution can correspond to an initial volume of infusion, if the image is sufficiently close to the infusion. Alternatively or additionally, the image can encompass diffusion of the viral vector into the tissue at some time period following the initial delivery of the vector. The evaluator 228 can co-register the estimated volume of distribution 206 and/or the estimated volume of transfection 220 relative to the actual volume ascertained from the imaging data 230.

The evaluator 228 can also compare the actual and estimated volumes to provide an indication of one or more of the estimated volumes. For example, the evaluator 228 can also include an adjustment control 232 that can be utilized to modify one or more of the models, such as including the fluid delivery model and the transfection model, to improve the accuracy of the model according to the comparison of the actual and estimated volumes. Since the actual data for a given patient that characterizes the volume of distribution and/or transfection, the evaluator 228 can output the actual volume of distribution indicated at 234. The actual volume of distribution can be used to compute a volume of transfection, which can be utilized for estimating the spread of optical stimulation such as shown and described herein.

As a further example, the viral vector can be a bicistronic lentivirus that can express the desired channelrhodopsin-2 protein intracellularly as well as express a marker (intracellular or extracellular) that can be visible via one or more imaging modalities. In this way, calculations can be made accurately to determine the volume of transfection based on the actual volume of distribution with certain assumptions being made that the markers expressed in equal or proportional quantities to the channelrhodopsin-2 protein in the given cells. Alternatively or additionally, the viral vector can include an extracellular tag that can be detected in the imaging data for use in calculating an actual volume of distribution resulting from infusion and/or diffusion of the vector.

Figure 14:
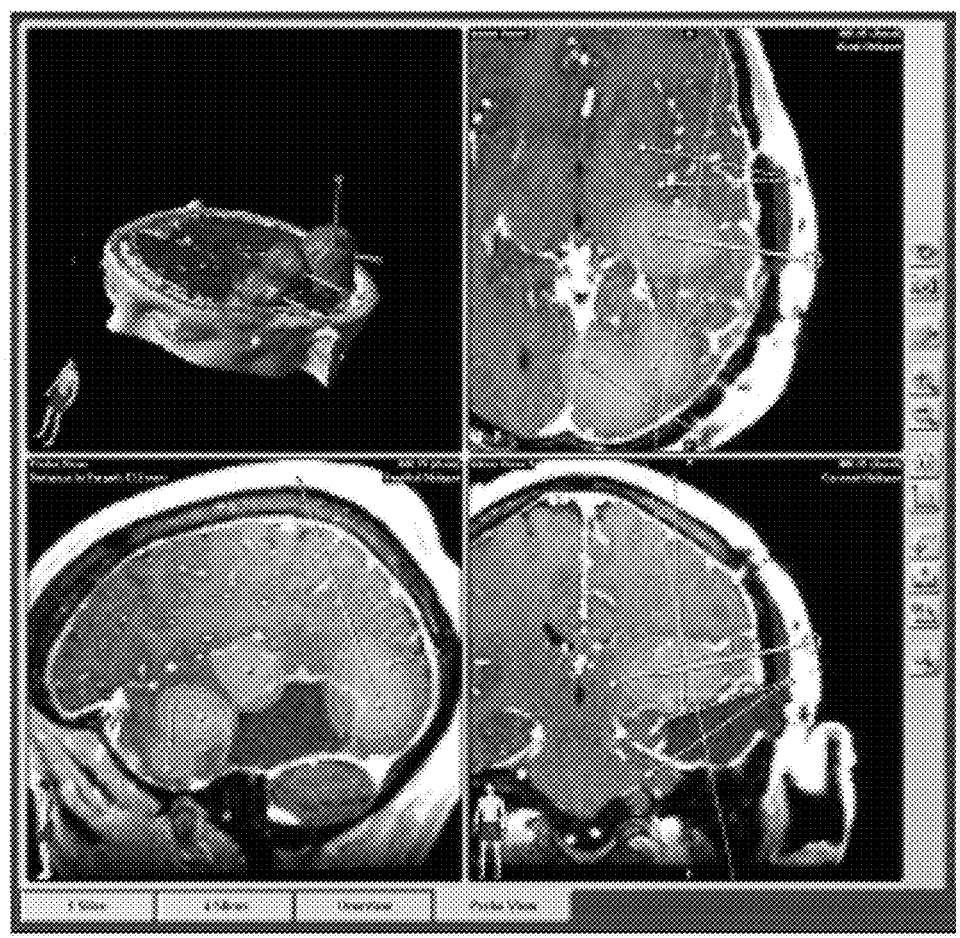
FIG. 14 depicts examples of a fluid model demonstrating graphical representations of infusion and diffusion of a solution.

FIG. 14 demonstrates an example of graphical renderings that can be utilized to show fluid dynamics, including a volume of distribution for infusion within a patient's brain. In the example of FIG. 14, several images are shown with different catheters for different trajectories for such catheters and the corresponding simulated infusion volumes. The simulated infusion volumes shown can be calculated and used as part of the workflow, such as disclosed with respect to FIG. 13.

Figure 15:
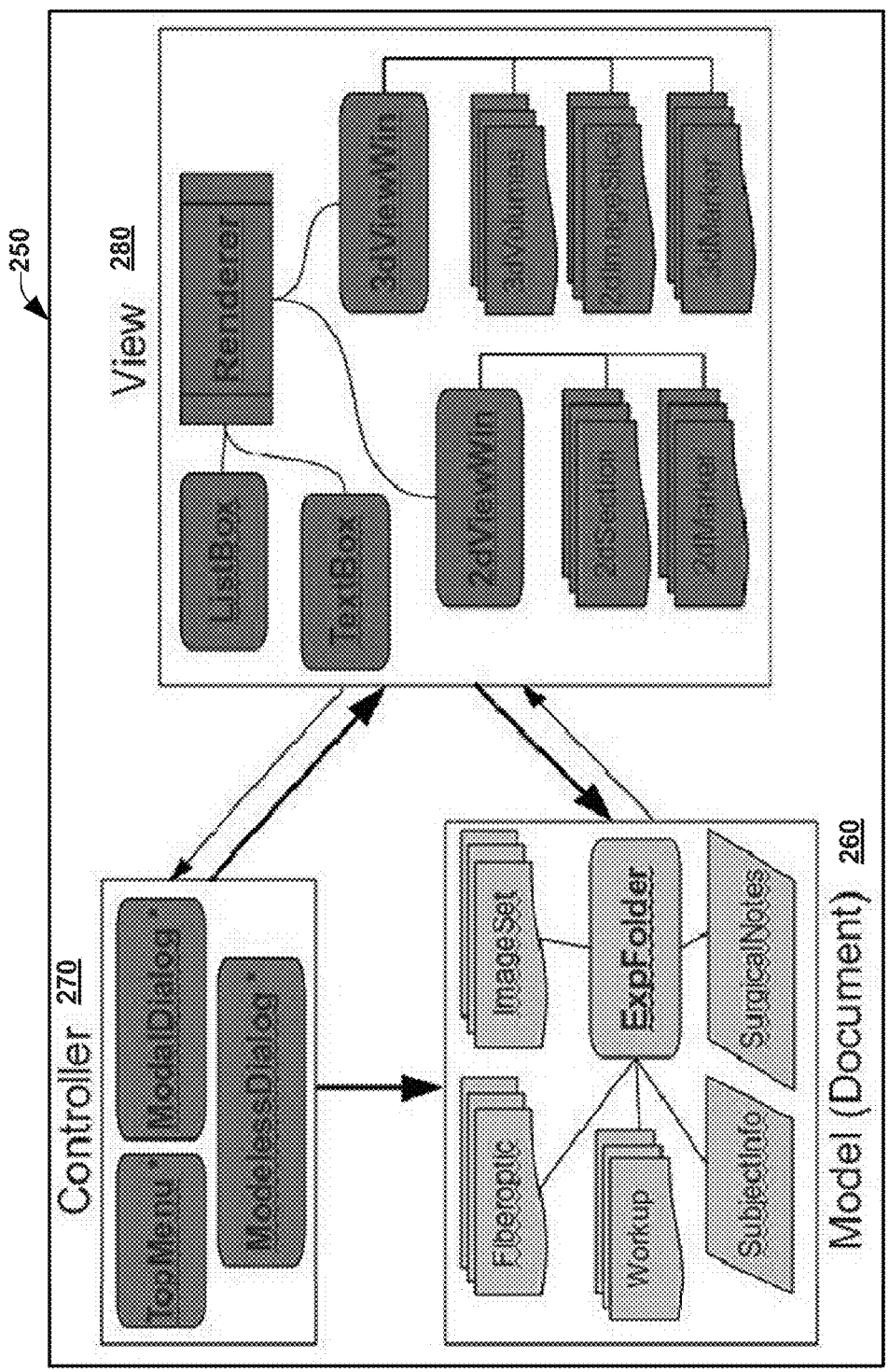
FIG. 15 depicts an example of a system architecture that can be used to implement a tool.
Figure 16:
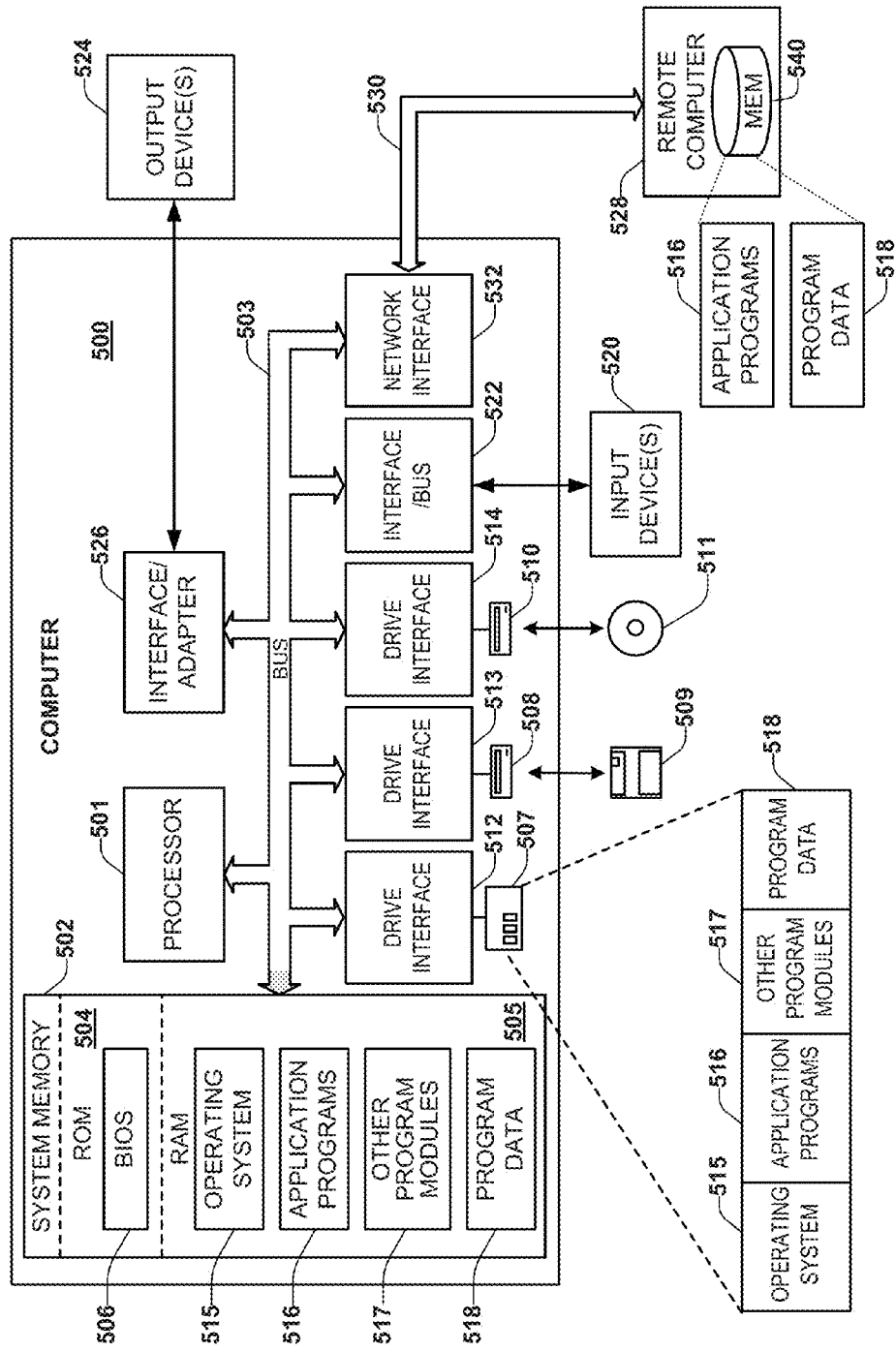
FIG. 16 depicts an example computer environment that can be used to perform methods and processes according to embodiments of the invention.

FIG. 15 demonstrates an example of a model-view-control architecture 250 that can be implemented on a computer (e.g., corresponding to the user interface 38 and tool 22 of FIG. 2). The architecture 250 thus can include a model component 260, a controller component 270 and a view component 280, each of which can include an arrangement of objects programmed with instructions, which when executed by a processor implement various functions and methods. The model component 260 can be a domain-specific representation of data on which the analysis and planning tool (e.g., the tool 22 of FIG. 2) may operate. The view component 270 corresponds to the code that renders the model into a graphical user interface section. The controller component 280 receives user inputs and initiates a response by interacting and communicating with the model objects of the model component 260. The view objects can control the visual display of the model data that is represented in the graphical user interface. The controller objects can further implement menus and dialogs, such as to enable the user to manipulate the state of the model and the configuration of the displayed view.

It will be appreciated that portions of the invention used to determine a target VTDI or otherwise utilize the target VTDI may be embodied as a method, data processing system, or computer program product. Accordingly, these embodiments of the present invention may take the form of an entirely hardware embodiment, an entirely software embodiment, or an embodiment combining software and hardware, such as shown and described with respect to the computer system of FIG. 9. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, flash storage devices and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other processor-based apparatus provide steps for implementing the functions specified in the block or blocks.

In view of the foregoing, FIG. 9 illustrates one example of a computer system 500 that can be employed to execute one or more embodiments of the invention by storing and/or executing computer executable instructions. Computer system 500 can be implemented on one or more general purpose networked computer systems, embedded computer systems, routers, switches, server devices, client devices, various intermediate devices/nodes or stand alone computer systems. Additionally, computer system 500 can be implemented on various mobile clients such as, for example, a personal digital assistant (PDA), laptop computer, pager, and the like, provided it includes sufficient processing capabilities.

Computer system 500 includes processing unit 501, system memory 502, and system bus 503 that couples various system components, including the system memory, to processing unit 501. Dual microprocessors and other multi-processor architectures also can be used as processing unit 501. System bus 503 may be any of several types of bus structure including a memory bus or memory controller, a peripheral bus, and a local bus using any of a variety of bus architectures. System memory 502 includes read only memory (ROM) 504 and random access memory (RAM) 505. A basic input/output system (BIOS) 506 can reside in ROM 504 containing the basic routines that help to transfer information among elements within computer system 500.

Computer system 500 can include a hard disk drive 507, magnetic disk drive 508, e.g., to read from or write to removable disk 509, and an optical disk drive 510, e.g., for reading CD-ROM disk 511 or to read from or write to other optical media. Hard disk drive 507, magnetic disk drive 508, and optical disk drive 510 are connected to system bus 503 by a hard disk drive interface 512, a magnetic disk drive interface 513, and an optical drive interface 514, respectively. The drives and their associated computer-readable media provide nonvolatile storage of data, data structures, and computer-executable instructions for computer system 500. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the present invention.

A number of program modules may be stored in drives and RAM 505, including operating system 515, one or more application programs 516, other program modules 517, and program data 518. The application programs and program data can include functions and methods programmed to estimate spread of optical stimulation as well as design parameters for stimulation of VTDI in a given patient, such as shown and described herein (e.g., FIGS. 1-15).

A user may enter commands and information into computer system 500 through one or more input devices 520, such as a pointing device (e.g., a mouse, touch screen), keyboard, microphone, joystick, game pad, scanner, and the like. For instance, the user can employ input device 520 to edit or modify a domain model. Additionally or alternatively, a user can access a user interface via the input device to create one or more instances of a given domain model and associated data management tools, as described herein. These and other input devices 520 are often connected to processing unit 501 through a corresponding port interface 522 that is coupled to the system bus, but may be connected by other interfaces, such as a parallel port, serial port, or universal serial bus (USB). One or more output devices 524 (e.g., display, a monitor, printer, projector, or other type of displaying device) is also connected to system bus 503 via interface 526, such as a video adapter.

Computer system 500 may operate in a networked environment using logical connections to one or more remote computers, such as remote computer 528. Remote computer 528 may be a workstation, computer system, router, peer device, or other common network node, and typically includes many or all the elements described relative to computer system 500. The logical connections, schematically indicated at 530, can include a local area network (LAN) and a wide area network (WAN).

When used in a LAN networking environment, computer system 500 can be connected to the local network through a network interface or adapter 532. When used in a WAN networking environment, computer system 500 can include a modem, or can be connected to a communications server on the LAN. The modem, which may be internal or external, can be connected to system bus 503 via an appropriate port interface. In a networked environment, application programs 516 or program data 518 depicted relative to computer system 500, or portions thereof, may be stored in a remote memory storage device 540.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A computer-implemented method for estimating a volume of tissue directly influenced (VTDI) by optogenetic stimulation comprising:
    storing, in memory an estimated volume distribution in tissue for a viral vector designed to express a light-responsive protein, wherein the estimated volume is based on a simulation or an image of distribution of the viral vector in tissue;
    computing, by a processor, an estimate of a volume of tissue directly influenced (VTDI) based on 1) the estimated volume of distribution in tissue, and 2) a light-neuron model that includes a multi-compartment neuron model, a multi-state ion channel model or ion pump model, and a light distribution model;
    repeatedly solving the light-neuron model over a plurality of model conditions to provide respective estimates of the VTDI in which a parameter space is varied, the parameter space comprising at least one of light pulse duration parameters, intensity of light source parameters, light source placement parameters, light distribution model parameters, source to neuron depth parameters, axon diameter parameters and neuron model parameters; and
    comparing the respective estimates of VTDI with a target VTDI to ascertain a set of output parameters for the parameter space corresponding to at least one of the respective estimates of VTDI for implementing the optogenetic stimulation to achieve the target VTDI.

2. The method of claim 1, wherein the computing further comprises computing an expression for the threshold for activation of the given neuron as a function of light source and stimulation parameters applied to a neuron type and photon sensitive channel characteristics defined by the light-neuron model.

3. The method of claim 1, wherein the computational model parameterizing a light-responsive ion channel, the ion channel model including parameters representing a an open state and a closed state of molecules in the VTDI and transitions between the open state and the closed state of the molecules in the VTDI, the computing including calculating an instantaneous rate of change between at least the open state and the closed state of the modules in the VTDI, the instantaneous rate of change being based on the simulation of activation and deactivation of light of the tissues that includes the VTDI.

4. The method of claim 1, wherein the repeatedly solving further comprises repeatedly solving the light-neuron model to compute a threshold source irradiance to inhibit action potentials for each respective neuron in each respective estimate of VTDI.

5. The method of claim 1, further comprising a computational model parameterizing at least one of a light-driven ion channel or a light-driven pump model, the computational model including parameters representing a plurality of states and transitions between the plurality of states, the computing including calculating an instantaneous rate of change for at least some of the plurality of states, the instantaneous rate of change being dynamically dependent on light irradiance.

6. The method of claim 5, wherein the at least one microbial op sin model being inserted into at least some compartments of the neuron model.

7. The method of claim 6, wherein the at least one microbial opsin model is selectively inserted into different compartments of the neuron model in different density distributions that vary depending on a type of each compartment.

8. The method of claim 6, wherein the at least one microbial opsin model is inserted into different compartments of the neuron model in different density distributions based on an estimated distance from a soma.

9. The method of claim 6, wherein the at least one microbial opsin model is inserted into different compartments of the neuron model in a density distributions that varies as a function of axon diameter.

10. The method of claim 1, further comprising a plurality of different types of neuron models representing different types of neurons, a given type of neuron model being selected in response to a user input.

11. The method of claim 1, wherein the light-neuron model comprises a light-axon model, the light-axon model comprising:
  a multi-compartment axon model;
  a multi-state microbial opsin model, which is inserted into the multi-compartment axon model; and
  a light distribution model, the computing comprising solving the model to compute a threshold source irradiance to initiate action potential for each respective axon.

12. The method of claim 11, further comprising:
  repeatedly solving the light-neuron model over a plurality of model conditions to provide the respective estimates of the VTDI in which at least one of light pulse duration parameters, source to neuron depth parameters, axon diameter parameters and microbial opsin model parameters are varied; and
  comparing the respective estimates of VTDI with a target VTDI to ascertain threshold of irradiation.

13. The method of claim 12, further comprising quantitatively independently varying a density of microbial opsin expression and associated ion channel or ion pump conductivity.

14. The method of claim 11, wherein the ion channel model further comprises a computational model having parameters programmed to represent a density of ion channels inserted in the neural process that varies as a function of neural process diameter.

15. The method of claim 14, wherein the computational model having parameters programmed to represent a density of ion channels comprises a uniform expression model or a neural process diameter dependent expression.

16. The method of claim 1, the light-neuron model further comprising:
  a neuron model comprises morphologic parameters and electrical parameters of ion channels; and
  a microbial opsin model that includes parameters representing at least three states, transitions between at least some of the states; and
  the light distribution model including parameters representing scattering and absorbance of light.

17. The method of claim 16, wherein the microbial opsin model comprises at least four states, a rate of change between at least two of the states varying dynamically as a function of an activation rate constant that further depends on light irradiance.

18. The method of claim 16, wherein the microbial opsin model comprises a computational model representing a density of microbial opsin that varies as a function of neural process diameter.

19. The computer-implemented method of claim 2, wherein the computing further comprises computing an activation threshold for cells targeted by a viral vector based on parameters of the light-neuron model representing properties of the light responsive protein, optical properties of tissue, and the light source configuration.

20. The method of claim 1, wherein the light-neuron model further comprises:
  a microbial opsin model; and
  wherein the parameter space includes parameters representing density of photon-sensitive channels, the density being uniformly or non-uniformly distributed in the neuron model in response to a user input.

21. A non-transitory computer-readable medium comprising instructions executable by a processor, the instructions comprising:
  a computational light-neuron model comprising:
    a multi-compartment neuron model; and
    at least one of a multi-state ion channel model or a pump model, which is inserted into the neuron model and includes parameters representing states and transitions between states; and
    a light distribution model that parameterizes irradiance from a light source on the neuron model;
  an estimator programmed to repeatedly solve the computational light-neuron model over a plurality of model conditions by varying a set of model parameters for the computational light-neuron model over a parameterization space and to provide respective estimates of a volume of tissue directly influenced (VTDI) based on an estimated volume of transfection in tissue for a viral vector designed to express a light-responsive protein, each respective estimate of VTDI including a set of respective model parameters for the computational light-neuron model, the estimator further programmed to compare the respective estimates of VTDI with a target VTDI to determine a set of output parameters for the parameterization space to control stimulation achieve the target VTDI; and
  the set of output parameters for the parameterization space being stored in memory.

22. The medium of claim 21, wherein the estimator further is programmed to compute the estimated VTDI based on the volume of transfection, the volume of transfection being calculated from at least one of simulation or imaging data.

23. The medium of claim 22, wherein the estimator further is programmed to compute an estimate of spread of the optogenetic stimulation.

24. The medium of claim 21, wherein the estimator further is programmed to solve the light-neuron model to compute a threshold source irradiance to initiate an action potential for each respective neuron in the estimated VTDI.

25. The medium of claim 21, wherein the at least one ion channel model or pump model further comprises a microbial opsin model that includes parameters representing at least three states, transitions between at least some of the states and a density of microbial opsin inserted in the neuron model.

26. The medium of claim 25, wherein the parameters representing the density of the microbial opsin are uniformly or non-uniformly distributed in respective compartments of the neuron model in response to a user input.

27. The medium of claim 21, further comprising a plurality of different types of neuron models, a given type of neuron model being selected and utilized by the estimator for computing the set of output parameters in response to a user input.

28. The medium of claim 21, wherein the estimator further is programmed to solve the light-neuron model to compute a threshold source irradiance to inhibit action potentials for each neuron in the set of neurons.

29. The medium of claim 21 wherein the light-neuron model further comprises a light-axon model, the light-axon model comprising:
    a multi-compartment axon model;
    a multi-state photon-responsive ion channel model or photon-sensitive pump model, which is inserted into the axon model; and
    a light distribution model, the estimator being programmed to solve the model by computing model parameters to provide a threshold source irradiance to initiate an action potential for the light-axon model.

30. The medium of claim 21 wherein the light-neuron model further comprises a light-axon model, the light-axon model comprising:
    a multi-compartment axon model;
    a multi-state photon-responsive opsin model, which is inserted into the axon model; and
    a light distribution model, the estimator being programmed to solve the model by computing model parameters to provide a threshold source irradiance to inhibit action potentials for the light-axon model.

* * * * *